(12) United States Patent
Auld et al.

(10) Patent No.: US 11,701,254 B2
(45) Date of Patent: Jul. 18, 2023

(54) SOFT TIP CANNULA WITH RETRACTABLE TIP PROTECTOR

(71) Applicant: ALTAVIZ, LLC, Irvine, CA (US)

(72) Inventors: Jack R. Auld, Laguna Niguel, CA (US); Matthew Flowers, Aliso Viejo, CA (US); Tammo Heeren, Aliso Viejo, CA (US); Hien Nguyen, Westminster, CA (US); John C. Huculak, Mission Viejo, CA (US); Eric Anderfaas, Westminster, CA (US)

(73) Assignee: ALTAVIZ, LLC, Irvine, CA (US)

( * ) Notice: Subject to any disclaimer, the term of this patent is extended or adjusted under 35 U.S.C. 154(b) by 0 days.

(21) Appl. No.: 17/100,845

(22) Filed: Nov. 21, 2020

(65) Prior Publication Data
US 2021/0154046 A1    May 27, 2021

Related U.S. Application Data

(60) Provisional application No. 62/938,854, filed on Nov. 21, 2019.

(51) Int. Cl.
*A61F 9/00* (2006.01)
*A61M 5/32* (2006.01)
*A61M 5/34* (2006.01)

(52) U.S. Cl.
CPC ......... *A61F 9/0008* (2013.01); *A61M 5/3202* (2013.01); *A61M 5/3204* (2013.01);
(Continued)

(58) Field of Classification Search
CPC . A61F 9/0008; A61M 5/3202; A61M 5/3204; A61M 5/3293; A61M 5/347;
(Continued)

(56) References Cited

U.S. PATENT DOCUMENTS 3,630,198 A     12/1971 Henkin
4,581,024 A *    4/1986 Swenson ............... A61M 5/343
                                                  604/272

(Continued)

OTHER PUBLICATIONS

Korean Intellectual Property Office, Authorized Officer Jung, Da Won, International Search Report and Written Opinion for corresponding International application No. PCT/US2020/061695, dated Mar. 15, 2021, 11 pages.
(Continued)

*Primary Examiner* — Theodore J Stigell
*Assistant Examiner* — Rachel T. Smith
(74) *Attorney, Agent, or Firm* — William A. English; Vista IP Law Group LLP

(57) ABSTRACT

Injector devices and methods for using them to deliver medicament into a patient's body, e.g., sub-retinally within an eye, are provided. The injector includes an injector cannula having a soft injector tip. A retractable tip protector tube is slidably disposed on the flow cannula between an extended position in which the tip protector tube covers the entire injector tip, and a retracted position in which the tip protector tube is retracted proximally thereby exposing at least part of the injector tip. Accordingly, the tip protector tube protects the injector tip from being damaged while advancing the injector tip to a target injection site.

34 Claims, 22 Drawing Sheets

(52) U.S. Cl.
CPC ........ *A61M 5/3286* (2013.01); *A61M 5/3293* (2013.01); *A61M 5/343* (2013.01); *A61M 5/347* (2013.01); *A61M 5/348* (2013.01); *A61M 2205/0216* (2013.01)

(58) Field of Classification Search
CPC ........ A61M 2210/0612; A61M 5/3243; A61M 31/00; A61M 1/00; A61M 25/00; A61M 2025/0042; A61M 25/0067; A61M 2025/0081; A61M 25/0612; A61M 5/349; A61B 2017/22041

See application file for complete search history.

(56) References Cited

U.S. PATENT DOCUMENTS

| | | | |
|---|---|---|---|
| 5,718,689 A * | 2/1998 | Stevenson | A61M 5/3205 128/919 |
| 6,494,892 B1 | 12/2002 | Ireland | |
| 9,387,309 B2 | 7/2016 | Parodi et al. | |
| 2012/0177436 A1* | 7/2012 | LaBombard | A61M 25/0097 403/109.1 |
| 2017/0216092 A1* | 8/2017 | Singh | A61M 25/01 |
| 2018/0296391 A1* | 10/2018 | Charles | A61M 1/7415 |

OTHER PUBLICATIONS

Jung, Da Won, Korean Intellectual Property Office, International Search Report and Written Opinion for corresponding International Application No. PCT/US2020/061695, dated Mar. 15, 2021, 11 pages.

* cited by examiner

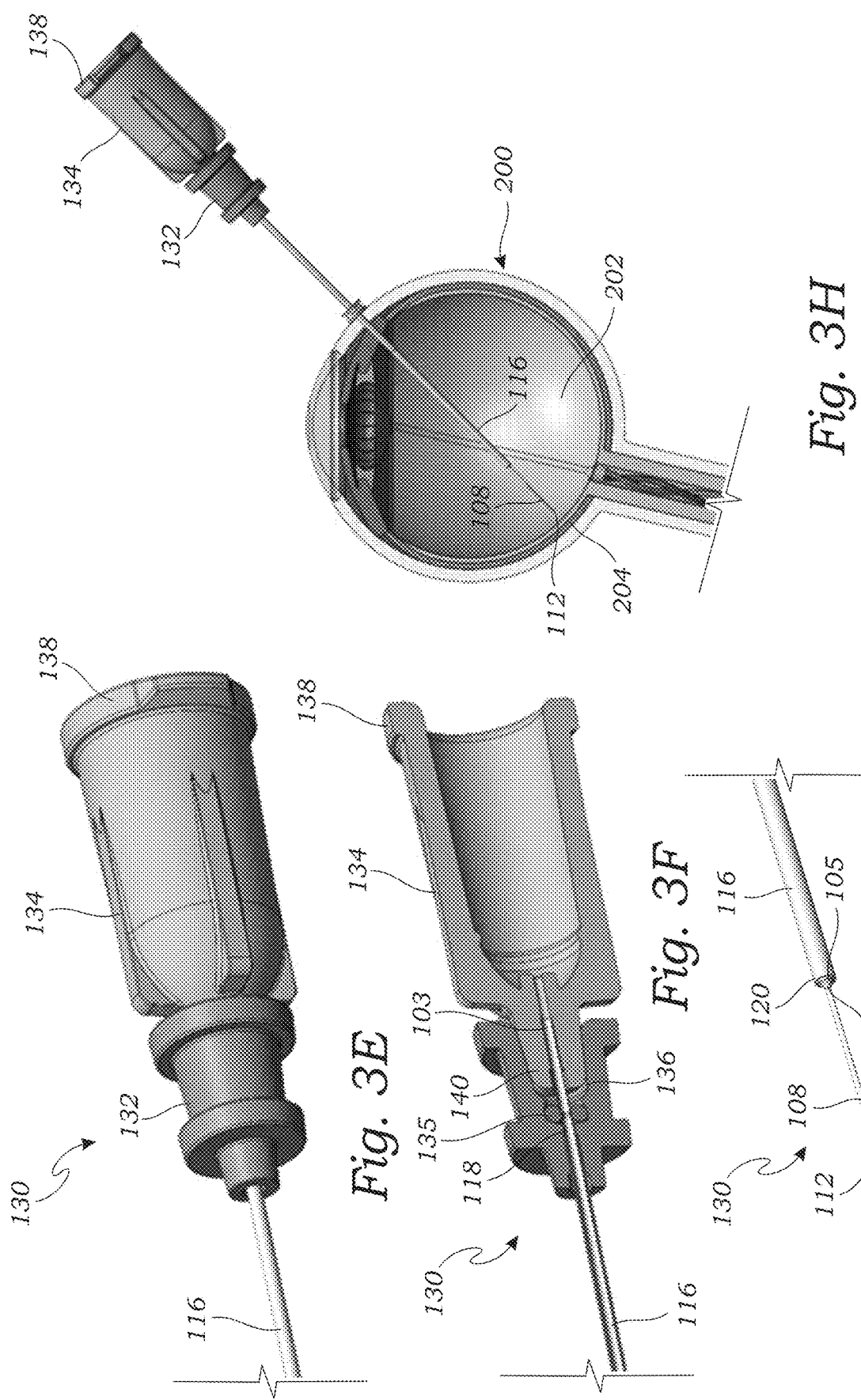

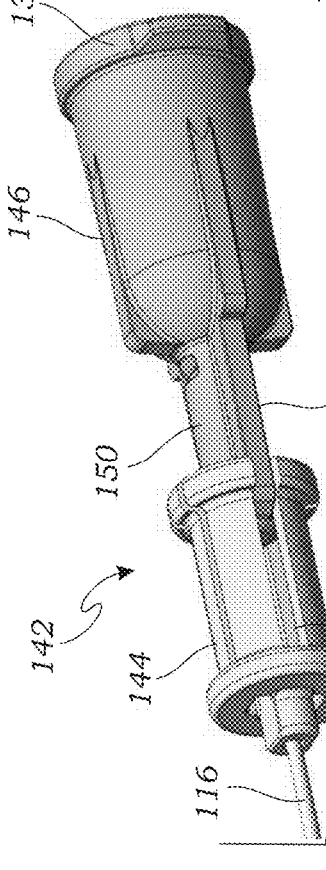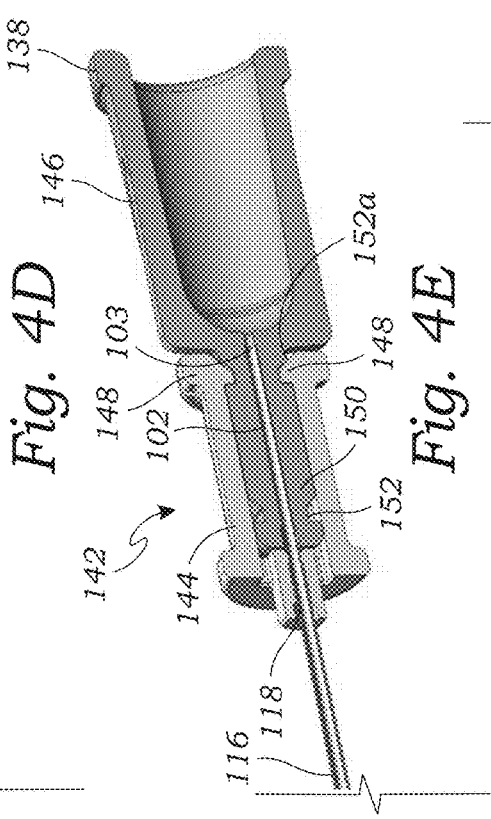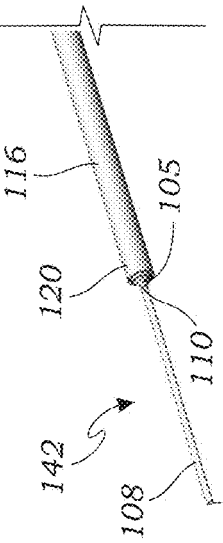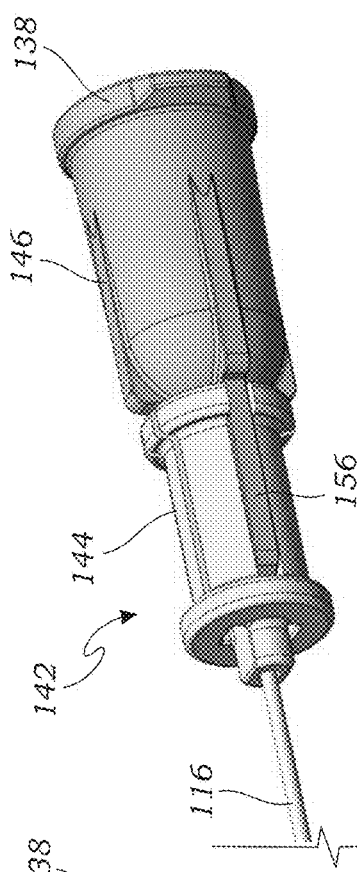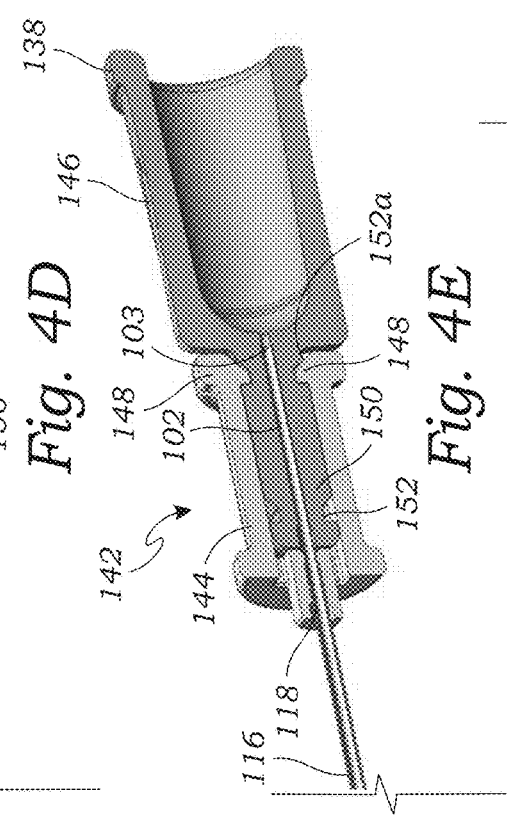

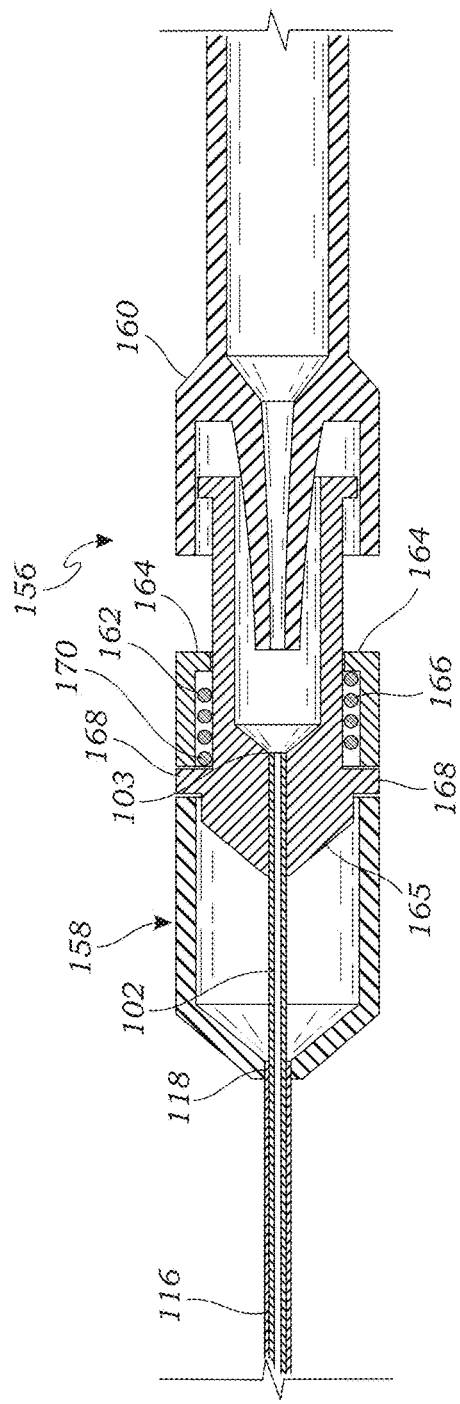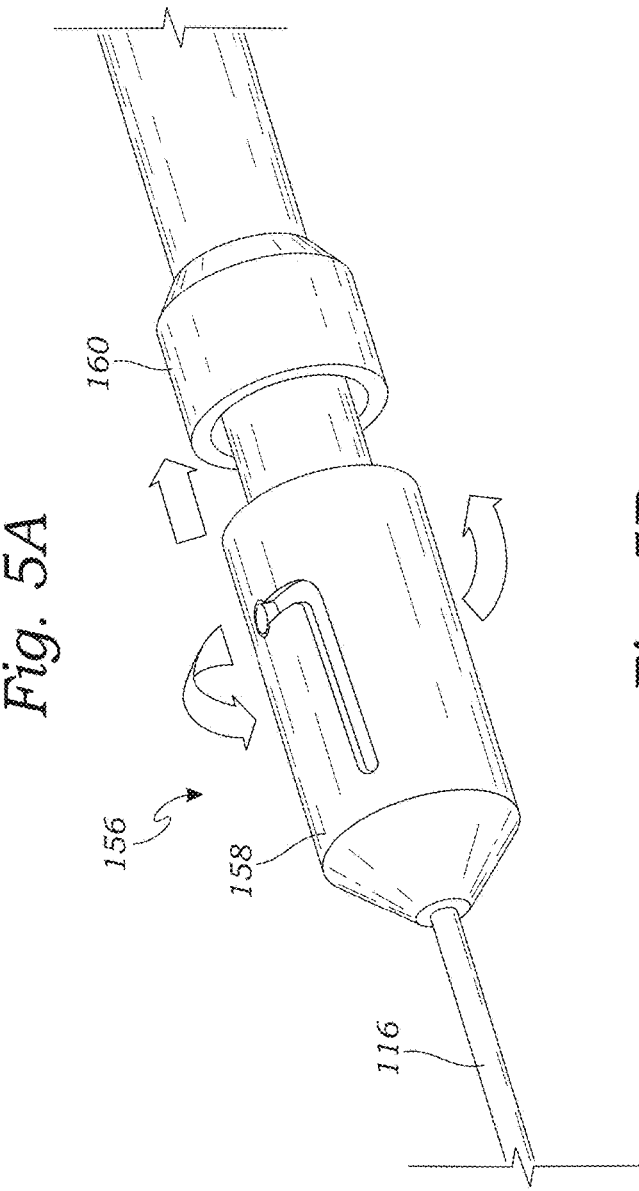

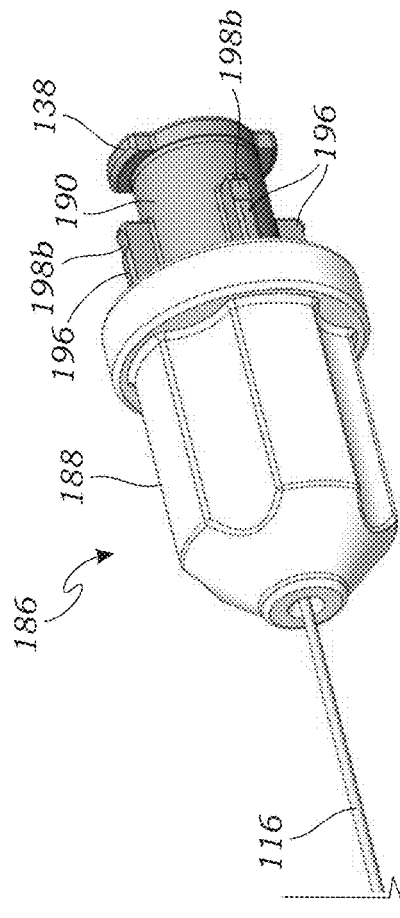
Fig. 7A
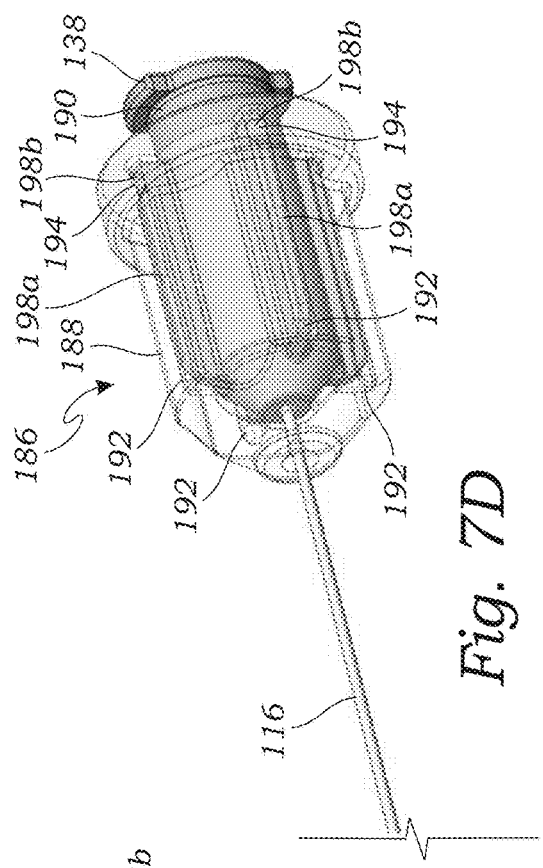
Fig. 7D
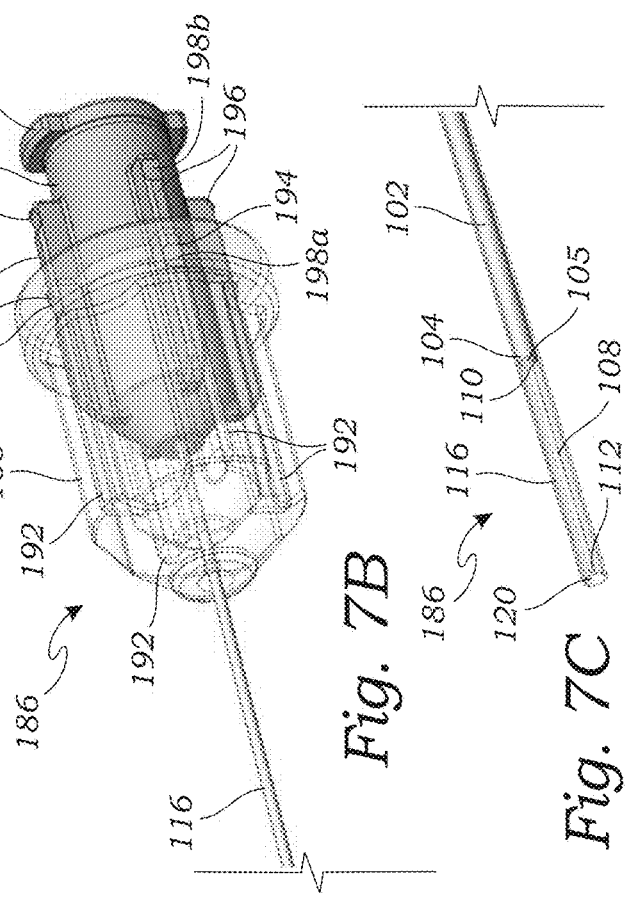
Fig. 7B
Fig. 7C
Fig. 7E

SOFT TIP CANNULA WITH RETRACTABLE TIP PROTECTOR

RELATED APPLICATION DATA

The present application claims benefit of co-pending provisional application Ser. No. 62/938,854, filed Nov. 21, 2020, the entire disclosure of which is expressly incorporated by reference herein.

FIELD OF THE INVENTION

The present invention relates to devices and methods for delivering agents into a patient's body and, more particularly, to injector cannulas having flexible tips for delivering agents, e.g., fluidic medicaments, and to methods for using such injectors.

BACKGROUND

Injections of medicaments into certain parts of a body require a very fine gauge needle (or other injector tip), such as injections into small anatomies and/or delicate tissues. For example, sub-retinal injections are a delicate procedure in which a very fine gauge needle or injector tip is utilized to minimize damage to the retinal tissues and to facilitate precise targeting of the injection site. Injectors for such micro-injections generally comprise a cannula which is connectable to a syringe or other injector device for providing a pressurized source of medicament.

Current cannulas for micro-injections, such as sub-retinal injections, generally have a three piece construction: (1) a Luer taper hub for interfacing with a syringe; (2) a hollow stainless steel tube extending from the hub approximately 28 mm; and (3) a fine gauge hollow tip bonded within and extending from the distal end of the metal tube. The distal tip is typically constructed of polyimide tubing, having an outer diameter of approximately 38 to 41 gauge, equivalent to around 0.005" (0.13 mm), and a wall thickness of around 0.001" (0.03 mm), or smaller. The exposed length of the distal tip extension is typically about 2 mm to 5 mm, or longer. An injection tip of these dimensions and material is relatively flexible and is very susceptible to bending, kinking, or crushing. In particular, passing the flexible tip through a valved trocar cannula, commonly used in ophthalmic surgery, can be difficult to do without damaging the tip. The valved trocar cannulas used in micro-surgeries typically have a thin silicone septum over the cannula passage which prevents escape of fluid through the cannula when no instruments are present. This septum can be difficult to pass through with the flexible tip. Often a kink in the tip will result in restricted/blocked flow, increased injection forces, or inconsistent flow stream from the tip. Therefore a need exists to protect the flexible tip until just prior to performing the injection, including while advancing the tip to the injection site, such as through a trocar, other surgical device, or even tissue.

SUMMARY

The present invention is directed to injector cannulas for performing micro-injections, and to methods of using the same. In general, the injector cannula has a soft/flexible injector tip and a retractable tip protector which protects the injector tip from being damaged while advancing the injector tip to a target injection site.

In accordance with a first embodiment, an injector cannula for delivering a medicament into a patient's body comprises a flow cannula having a proximal end and a distal end. The flow cannula may be a tube (e.g., a metal tube, a plastic tube, etc.) having a lumen extending from the proximal end to the distal end. An injector fitting is disposed on the proximal end of the flow cannula. The injector fitting is configured to be coupled to a fluidic injector, such as a syringe or other fluidic injector device. The fluidic injector may then inject fluidic medicament through the lumen of the flow cannula.

A flexible injector tip having a proximal end and a distal end is coupled to the flow cannula, with the proximal end of the injector tip coupled to the distal end of the flow cannula. The injector tip is a tube having a very fine gauge (e.g., an outer diameter of about 38 to 41 gauge (about 0.005"=0.13 mm), or smaller, made from a polymer material, such as polyimide or other suitable polymer. The very fine gauge and polymer material results in a very flexible structure for the injector tip. The injector tip has a lumen which is in fluid communication with the lumen of the flow cannula, and the distal end of the injector tip has an opening for delivering medicament out through the opening.

A tip protector tube is slidably disposed on the flow cannula. The tip protector tube is slidable on the flow cannula from an extended position in which the tip protector tube covers the entire injector tip, and a retracted position in which the tip protector tube is retracted proximally thereby exposing at least part of the injector tip. The tip protector tube may be fully retractable from the injector tip, such that the entire length of the injector tip is outside of the tip protector tube (i.e., a distal end of the tip protector tube is proximal of the proximal end of the injector tip). The tip protector tube is substantially stiffer than the injector tip. For example, the tip protector tube has sufficient stiffness that it can be pushed through a valve of a trocar valve without bending or crushing such that it protects the injector tip from being damaged.

In another aspect of the injector cannula, the injector fitting may be a Luer hub. A Luer hub is a standardized hub connectable to a mating connector on a syringe or fluidic injector device, which provides a sealed connection (i.e., leak free connection).

In still another aspect, the injector cannula may further comprise a hub coupled to a proximal portion of the tip protector tube. The hub is slidably disposed on the flow cannula such that retracting the hub proximally retracts the tip protector tube.

In yet another aspect, the injector cannula may further include an elastomeric seal disposed on the hub through which the flow cannula passes. The seal provides a friction fit around the flow cannula and prevents leakage between the flow cannula and the tip protector sleeve. The elastomeric seal may be an O-ring seal, or other suitable seal.

In another aspect, the injector cannula may have retention mechanisms to retain the tip protector tube in the retracted position and/or extended position. In one example of retention mechanisms, the hub has a hub interface and the injector fitting has a fitting interface which mates with the hub interface. The hub interface and injector interface secure the hub to the injector fitting in the retracted position of the tip protector tube. In another aspect, the hub interface comprises a female tapered surface and the injector fitting interface comprises a male tapered surface.

In yet another aspect of the injector cannula, the hub has a plurality of snaps spaced apart longitudinally on the hub, and the injector fitting has a plurality of notches spaced apart longitudinally on the injector fitting. The snaps are configured to interface with respective notches on the injector fitting to retain the hub and tip protector tube separately in the extended position and the retracted position.

In another aspect, the hub and the injector fitting have a sliding interface which rotationally aligns the hub and the fitting and prevents relative rotation of the hub and fitting. For instance, the sliding interface may comprise a slot on one of the hub and the fitting and a ridge on the other of the hub and the fitting, such that the ridge is slidably received in the slot.

In still another aspect of the cannula injector, the hub has a raised feature on an inner diameter surface, and the injector fitting has at least two detents on an outer diameter surface. The raised feature is configured to interface with the at least two detents to retain the hub and tip protector tube in two different positions including the extended position and the retracted position.

In yet another aspect, the injector fitting has a groove on the outer diameter surface in which the raised feature is received such that the groove guides the raised feature along a path as the hub is moved relative to the injector fitting. In various additional aspects, the groove may extend in one of the following different paths, such as a helical path around the outer diameter surface of the injector fitting; a linear path extending longitudinally along the outer diameter surface; and a hook shaped path having a first portion extending circumferentially around the outer diameter surface and a second portion extending longitudinally along the outer diameter surface.

In yet another aspect of the injector cannula, one of the hub and the injector fitting has a plurality of ratchet grooves, and the other of the hub and the injector fitting has one or more retention arms. The retention arms interface with each of the ratchet grooves to retain the hub and tip protector tube in a plurality of different longitudinally spaced apart positions including the extended position and the retracted position.

In another aspect, the injector cannula further includes a retraction spring disposed between the hub and the injector fitting. The retraction spring biases the hub toward the retracted position. A locking mechanism is disposed between the hub and injector fitting and is configured to releasably lock the hub in the extended position of the tip protector tube. The locking mechanism may comprise a bayonet fitting between the hub and the injector fitting. The bayonet fitting has a locked position which retains the hub in the extended position of the tip protector tube, and an unlocked position which allows the retraction spring to retract the hub and tip protector tube to the retracted position.

In yet another aspect of the injector cannula, the flexible injector tip is attached to the proximal end of the flow cannula via a tip bond joint. The tip bond joint may be formed using an adhesive disposed in an annulus between the injector tip and the flow cannula.

In still another aspect of the first embodiment, the injector cannula may include an injector device coupled to the injector fitting. The injector device provides a pressurized source of medicament. The injector device may be a syringe, a self-powered injector, or other suitable injector.

In accordance with a second embodiment described herein, a method is provided for using the injector cannula of the first embodiment for delivering a medicament to a patient's body. An injector device filled with a medicament is attached to the injector fitting. The injector cannula is advanced into the patient's body with the tip protector tube in the extended position. In this way, the tip protector tube protects the injector tip from being damaged, such as being bent, kinked or crushed, as the injector cannula is advanced. The tip protector tube is then retracted to the retracted position to expose the injector tip. With the injector tip exposed, the injector tip is advanced into a target tissue within the patient's body. This may be done by advancing the entire injector cannula and injector device. The injector device is actuated to deliver the medicament out through the injector tip and into the target tissue. The injector cannula may include any one or more of the additional aspects of the injector cannula of the first embodiment, and the method may include steps associated with such additional aspects, as described herein.

In accordance with a third embodiment, another injector cannula for delivering a medicament into a patient's body is disclosed herein. This injector cannula is similar to the first embodiment, except that it utilizes a shorter tip protector tube which does not extend proximally to the injector fitting in the fully retracted position. In addition, at least partly to account for the shorter length of the tip protector tube, the tip protector tube includes a tip protector tube stop which is configured to contact a hard stop on the trocar cannula as the injector cannula is advanced through the trocar cannula. The cooperating stops also retract the tip protector tube from the extended position to the retracted position as the flow cannula and injection tip are advanced after the tip protector tube is stopped by the cooperating stops.

Accordingly, the injector cannula includes a flow cannula having a proximal end and a distal end defining a flow cannula length. An injector fitting is disposed on the proximal end of the flow cannula. The injector fitting is configured to be coupled to a fluidic injector. A flexible injector tip is disposed on the distal end of the flow cannula and extends distally from the flow cannula. The injector tip has a proximal end and a distal end defining a full length of the injector tip. A tip protector tube is slidably disposed on the flow cannula. The tip protector tube has a proximal end and a distal end defining a tip protector tube length. The tip protector tube is slidable on the flow cannula from an extended position in which the tip protector tube covers the entire injector tip, a retracted position in which the tip protector tube is retracted proximally thereby exposing at least part of the injector tip, and a fully retracted position in which the distal end of the tip protector tube is aligned with, or up to 0.1 mm proximal of, the proximal end of the injector tip such that the full length of the injector tip is exposed. The tip protector tube has a tip protector tube length such that in the fully retracted position the proximal end of the tip protector tube is located proximal of the injector fitting. The tip protector tube is substantially stiffer than the injector tip. For example, the tip protector tube has sufficient stiffness that it can be pushed through a valve of a trocar valve without bending or crushing such that it protects the injector tip from being damaged.

This third embodiment injector cannula allows the tip protector tube to be shorter than the tip protector tube of the first embodiment as the tip protector tube does not need to extend proximally to the injector fitting, and the tip protector tube is not advanced completely when advancing the flow cannula and injector tip all the way to the target tissue. In other words, the tip protector tube is advanced sufficiently through the trocar valve to protect the delicate injection tip as it is advanced through the trocar valve, and then the tip protector tube is stopped.

In other aspect of the third embodiment, the tip protector tube length is less than one half the flow cannula length, or less than 75% of the flow cannula length. In another aspect, the tip protector tube length is less than 150% of the full length of the injector tip.

In yet another aspect, injector cannula may also have a handle attached to the proximal end of the tip protector tube. The handle may comprise a flared portion of a proximal portion of the tip protector tube, or the handle may be a separate handle component attached to the tip protector tube.

In another aspect, the distal end of the tip protector tube may be configured to contact a hard stop of a trocar cannula to prevent further advancement of the tip protector tube into the trocar cannula. In yet another aspect, the tip protector tube may be configured to advance fully through a trocar cannula, and the injector cannula may include a protector tube stop coupled to the tip protector tube. The tip protector tube stop is configured to contact a hard stop of a trocar cannula upon inserting the injector cannula through the trocar cannula to prevent further advancement of the tip protector tube into the trocar cannula. The protector tube stop comprises a handle attached to the proximal end of the tip protector tube. For instance, the handle may be any of the handles described above.

In accordance with a fourth embodiment, a method is provided for using the injector cannula of the third embodiment for delivering a medicament to a patient's body. An injector device filled with a medicament is attached to the injector fitting. The injector cannula is advanced through a trocar cannula inserted into the patient's body with the tip protector tube in the extended position. The injector cannula is advanced until a tip protector tube stop contacts a hard stop on the trocar cannula preventing the further advancement of the tip protector tube through the trocar cannula. With the protector tube stop bearing against the hard stop, the flow cannula and injector tip are advanced through the tip protector tube and trocar cannula thereby retracting the tip protector tube to the retracted position. A tip of the injector tip is inserted into a target tissue within the patient's body. Finally, the injector device is actuated to deliver the medicament through the injector tip and into the target tissue.

In another aspect of the method of fourth embodiment, the tip protector tube stop may comprise the distal end of the tip protector tube, and the hard stop on the trocar cannula comprises a trocar tube of the trocar cannula.

In yet another aspect of the method, the tip protector tube stop may comprise a handle attached to the proximal end of the tip protector tube, and the hard stop on the trocar cannula comprises a hub of the trocar cannula.

In another aspect of any of the embodiments of the injector cannula, the tip protector tube may have a hypodermic bevel on the distal end of the tip protector tube. This allows the injector cannula to be used without a trocar cannula. With the tip protector tube locked in the extended position, the hypodermic bevel on the tip protector tube is used to pierce body tissue to insert the injector cannula into a body structure. Once the injector cannula is advanced to a desired position where the injector tip is not at risk of damage, the tip protector tube is released by releasing the lock, and retracted to the retracted position.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings, wherein like reference numerals refer to like elements and the description for like elements shall be applicable for all described embodiments wherever relevant. It is emphasized that, according to common practice, the various features and design elements of the drawings are not to-scale. On the contrary, the dimensions of the various features and design elements are arbitrarily expanded or reduced for clarity. Included in the drawings are the following figures:

FIG. 3E is a side, perspective view of a proximal portion of an injector cannula of FIG. 3A, with the tip protector tube in a retracted position, according to one embodiment;

FIG. 3F is a side, cut-away view of the proximal portion of the injector cannula of FIG. 3A with the tip protector tube in the retracted position;

FIG. 3G is a side, perspective view of the distal portion of the injector cannula of FIG. 3A with the tip protector tube in the retracted position;

FIG. 3H is side, cut-away view of a human eye illustrating a method of using the injector cannula of FIG. 3A for delivering a medicament into a patient's eye with the tip protector tube in the retracted position;

FIG. 4A is a side, perspective view of a proximal portion of an injector cannula having a cooperating hub and Luer fitting retention mechanism, with the tip protector tube in an extended position, according to another embodiment;

FIG. 4B is a side, cut-away view of the proximal portion of the injector cannula of FIG. 4A with the tip protector tube in an extended position;

FIG. 4C is a side, perspective view of the distal portion of the injector cannula of FIG. 4A with the tip protector tube in an extended position;

FIG. 4D is a side, perspective view of a proximal portion of an injector cannula of FIG. 4A, with the tip protector tube in a retracted position, according to one embodiment;

FIG. 4E is a side, cut-away view of the proximal portion of the injector cannula of FIG. 3A with the tip protector tube in the retracted position;

FIG. 4F is a side, perspective view of the distal portion of the injector cannula of FIG. 4A with the tip protector tube in the retracted position;

FIG. 5A is a side, cross-sectional view of a distal portion of an injector cannula having spring biased retraction mechanism for retracting the tip protector tube, according to one embodiment;

FIG. 5B is a side, perspective view of the injector cannula of FIG. 5A illustrating a bayonet fitting for retaining and actuating the retraction mechanism, according to one embodiment;

FIG. 7A is a side, perspective view of a proximal portion of an injector cannula having a cooperating hub and Luer fitting retention mechanism, with the tip protector tube in an extended position, according to another embodiment;

FIG. 7B is a side, cut-away view of the proximal portion of the injector cannula of FIG. 7A with the tip protector tube in an extended position;

FIG. 7C is a side, perspective view of the distal portion of the injector cannula of FIG. 7A with the tip protector tube in an extended position;

FIG. 7D is a side, perspective view of a proximal portion of an injector cannula of FIG. 7A, with the tip protector tube in a retracted position, according to one embodiment;

FIG. 7E is a side, perspective view of the distal portion of the injector cannula of FIG. 7A with the tip protector tube in the retracted position;

DETAILED DESCRIPTION OF THE EXEMPLARY EMBODIMENTS

Figure 1A:
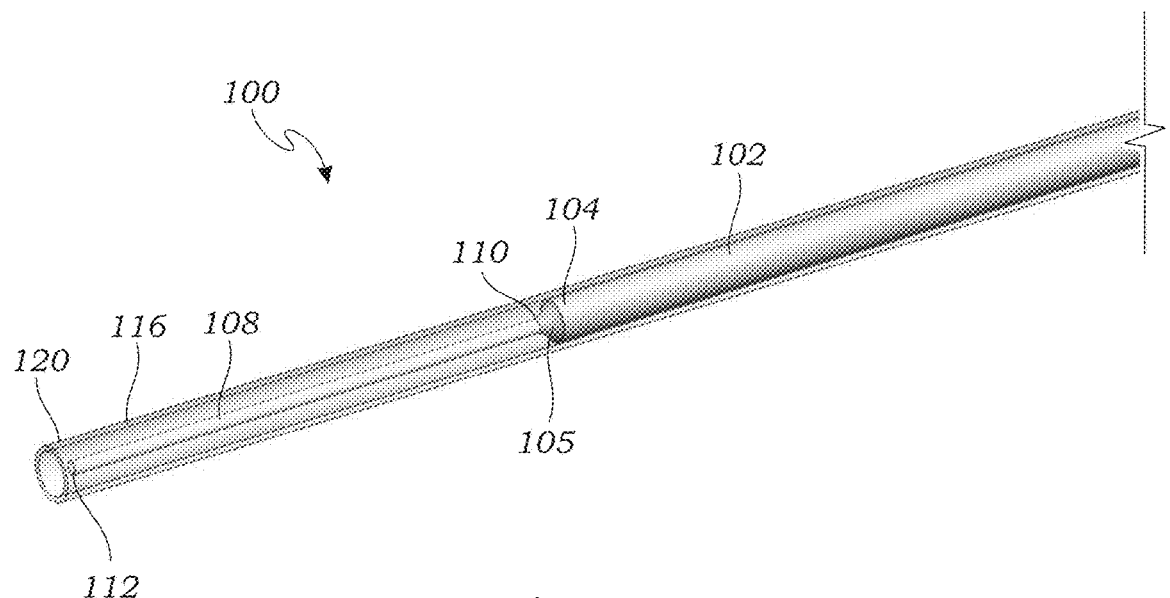
FIG. 1A is a side, perspective view of a distal portion of an injector cannula with a tip protector tube in an extended position, according to one embodiment.

Before the exemplary embodiments are described, it is to be understood that the invention is not limited to particular embodiments described, as such may, of course, vary. The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary, or the following detailed description. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It is noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

There are many applications where controlled delivery of a medicament using an injector cannula having a flexible injector tip, wherein it is desirable to protect the injector tip from being damages as it is positioned at a target injection site. The devices and methods described herein may be used for the delivery of medicaments into a patient's body, e.g., one or more viscous fluids or other flowable material for various therapeutic and/or diagnostic purposes. As used herein, "medicament" is intended to refer to any such fluids, agents, or materials, such as those described herein. For example, below is a summary of exemplary applications where the devices and methods described herein may be used to deliver fluids into a patient's body.

Ophthalmology: As depicted in FIGS. 2A-2D, 3D, and 11A-11D, the injector cannulas disclosed herein may be used for sub-retinal injections into the sub-retinal space 204 in the treatment of several disease conditions of an eye 200.

Treatment of retinal vein occlusions: Multiple indications may be treated by the administration of therapeutic agents into the sub-retinal space 204 in the eye 200, e.g., as shown in FIGS. 2A-2D, 3D, and 11A-11D. In cases of branch retinal vein occlusion (BRVO) and central retinal vein occlusion (CRVO), 50 to 150 µL of tissue plasminogen activator (TPA) may be administered through relatively small injection tips or needles (e.g., not more than 41 gauge) to dissolve blood clots formed by sub-retinal hemorrhages during the course of retinal surgery. In these cases, the ophthalmic surgeon may place the tip under the surface of a patient's retina and slowly inject the TPA to create a bleb of medicament that dissolves the coagulated blood over the course of a few days.

Gene therapy for the treatment of macular degeneration: Age-related macular degeneration (AMD) is a leading cause of vision loss and blindness among the elderly. AMD is a progressive ocular disease of the part of the retina, called the macula, which enables people to read, visualize faces, and drive. The disease initially causes distortion in central vision, and eventually leads to legal blindness. A layer of cells at the back of the eye, called the retinal pigment epithelium (RPE), provides support, protection, and nutrition to the light sensitive cells of the retina, i.e., the photoreceptors consisting of rods and cones. The dysfunction and/or loss of these RPE cells play a critical role in the loss of the photoreceptors and hence blindness in AMD. Recent advances in research show promise in new therapies to treat AMD. Human embryonic stem cells, gene therapies, complement factors, and viral vectors are under development with early stage animal studies and/or clinical trials. Some of these treatments require administration of the cells into targeted areas of the eye including the sub-retinal space or the suprachoroidal space with exquisite control over position, volumetric delivery rate, and/or total volume.

Figure 1B:
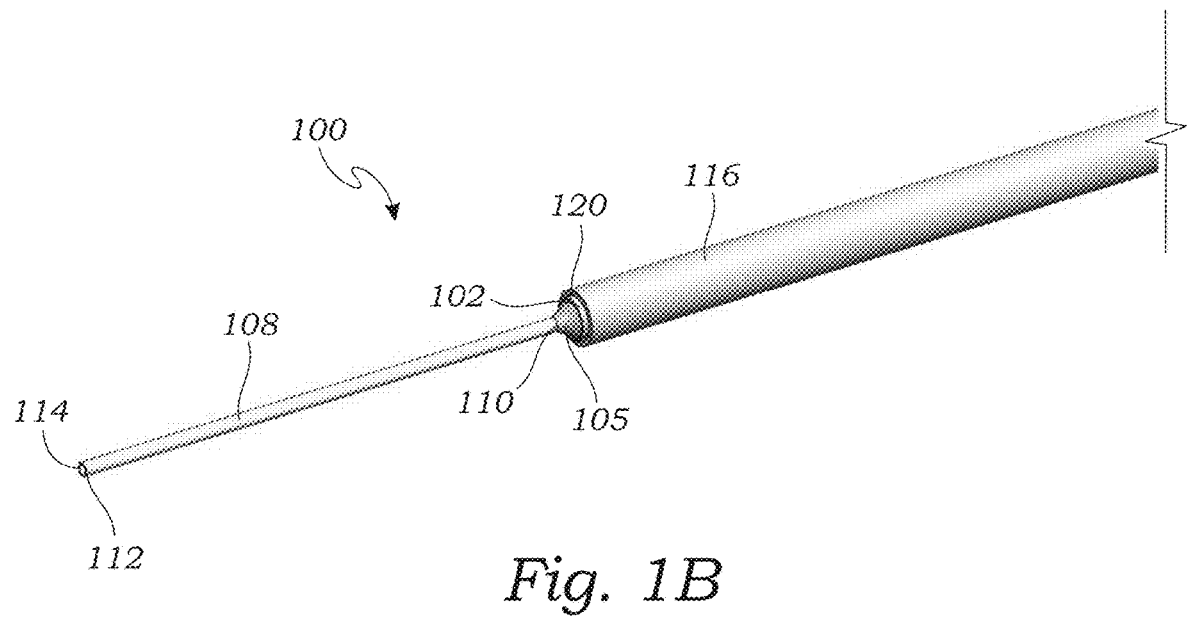
FIG. 1B is a side, perspective view of the distal portion of the injector cannula of FIG. 1A with the tip protector tube retracted to a retracted position, according to one embodiment.

Turning to FIGS. 1A-1B, one embodiment of an injector cannula 100 for delivering a medicament into a patient's body is illustrated. The injector cannula 100 includes a flow cannula 102 having a proximal end 103 (not shown in FIGS. 1A-1B, but see e.g., FIG. 3F) and a distal end 104. The flow cannula 102 is a tube having a lumen extending from the proximal end 103 to the distal end 104. The flow cannula 102 may be a metal tube, a plastic tube, or other suitable material. The flow cannula 102 may be a tube having a size in the range of 23 gauge to 27 gauge (e.g., for use in a sub-retinal injection), or other suitable size for the intended application.

A flexible injector tip 108 having a proximal end 110 and a distal end 112 is coupled to the flow cannula 102. The proximal end 110 of the injector tip 108 is attached to the distal end 104 of the flow cannula 102. The injector tip 108 is a tube typically having a very fine gauge, and has a smaller outer diameter than the inner diameter of the flow cannula 102. For instance, for use in sub-retinal injections or injections in small and/or delicate anatomical structures, the injector tip may have a size in the range of 38 to 41 gauge (about 0.005"=0.13 mm), or smaller, and a length of from 2 mm to 5 mm. The injector tip 108 may be attached to the flow cannula 102 using tip bond joint 105 comprising an adhesive disposed in the annulus between the outer diameter of the injector tip 108 and the inner diameter of the flow cannula 102. The injector tip 108 is made from a polymer material, such as polyimide or other suitable polymer. The very small diameter and polymer material of the injector tip 108 generally results in a very flexible, delicate, and somewhat fragile structure. The injector tip 108 has a lumen which is in fluid communication with the lumen of the flow cannula 102. The distal end 112 of the injector tip 108 has an opening 114 for delivering medicament out through the opening 114. The distal end 112 of the injector tip 108 may have a sharp tip or a tapered tip to facilitate the injector tip 108 penetrating into tissue to a target injection site.

A tip protector tube 116 is slidably disposed on the flow cannula 102. The tip protector tube 116 has a proximal end 118 (not shown in FIGS. 1A-1B, but see e.g., FIG. 3B) and a distal end 120. The tip protector tube 116 is a tube which receives the flow cannula 102 and injector tip 108 concentrically within the lumen of the tube. Accordingly, the tip protector tube 116 is a tube having a size large enough to receive the flow cannula 102 and injector tip 108 with its lumen. For instance, the tip protector tube 116 may be a tube formed of metal, polymer or other suitable material, having a size in the range of 23 gauge to 25 gauge (e.g., for use in a sub-retinal injection), or other suitable size for the intended application. As shown in FIGS. 1A-1B, the tip protector tube 116 is slidable on the flow cannula 102 between an extended position in which the tip protector tube covers the entire injector tip as shown in FIG. 1A, and a retracted position in which the tip protector tube is retracted proximally thereby exposing at least part of the injector tip as shown in FIG. 1B. FIG. 1B illustrates the injector cannula 100 with the tip protector tube 116 in a fully retracted position in which the entire length of the injector tip 108, is outside of the tip protector tube 116. In other words the distal end of the tip protector tube 16 is proximal of the proximal end 110 of the injector tip 108). The tip protector tube 116 is substantially stiffer than the injector tip 108. The tip protector tube 116 has sufficient stiffness that it can be pushed through a valve 124 of a trocar cannula 122 (see, e.g., FIG. 2A) without bending or crushing such that it protects the injector tip 108 from being damaged. The stiffness of the tip protector tube 116 may be accomplished by using a tube wall thickness and/or material which provides the required stiffness.

Figure 2A:
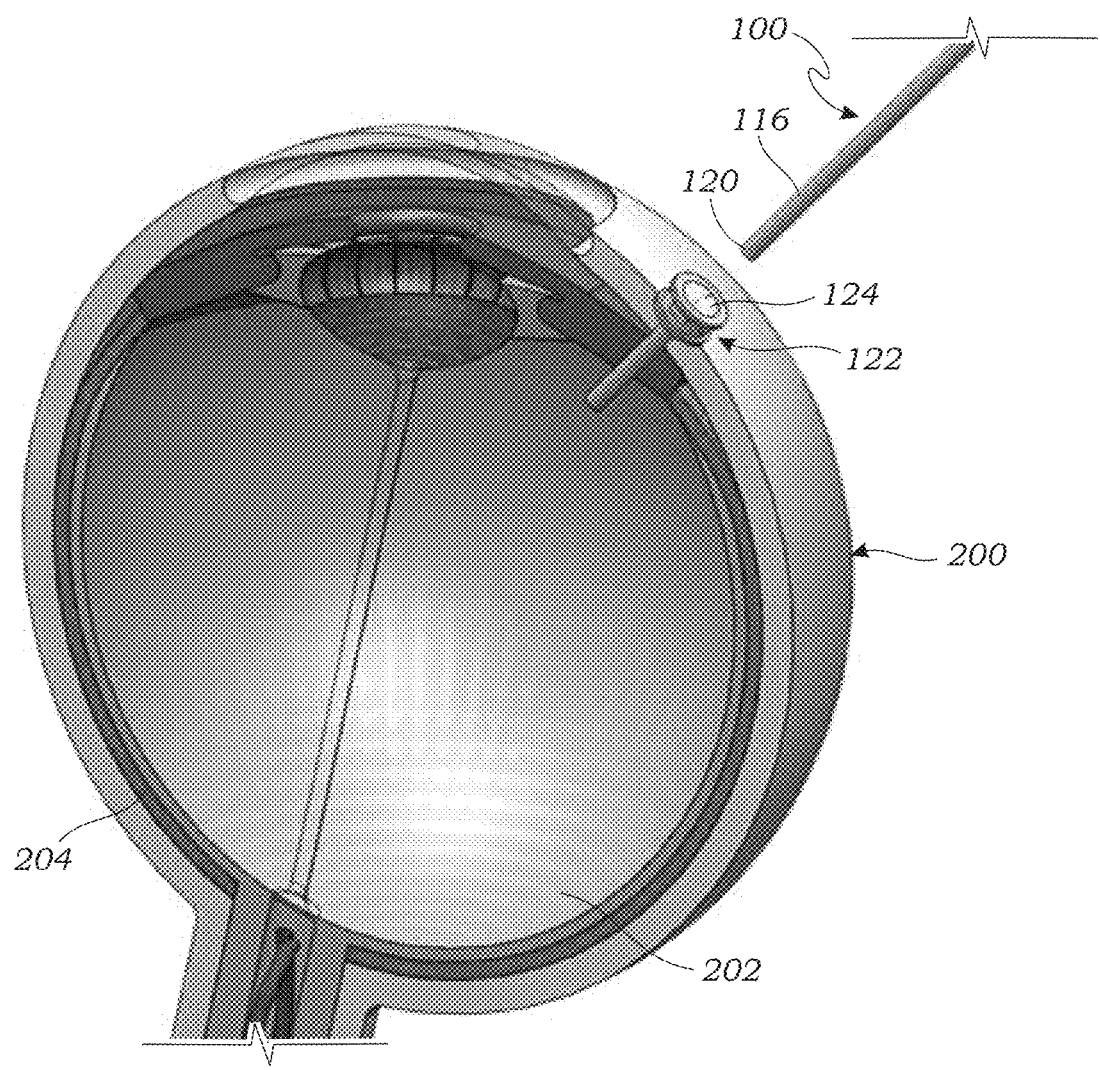
FIGS. 2A-2D are side, cut-away views of a human eye illustrating a method of using the injector cannula of FIGS. 1A-1B for delivering a medicament into a patient's eye, according to one embodiment.
Figure 15:
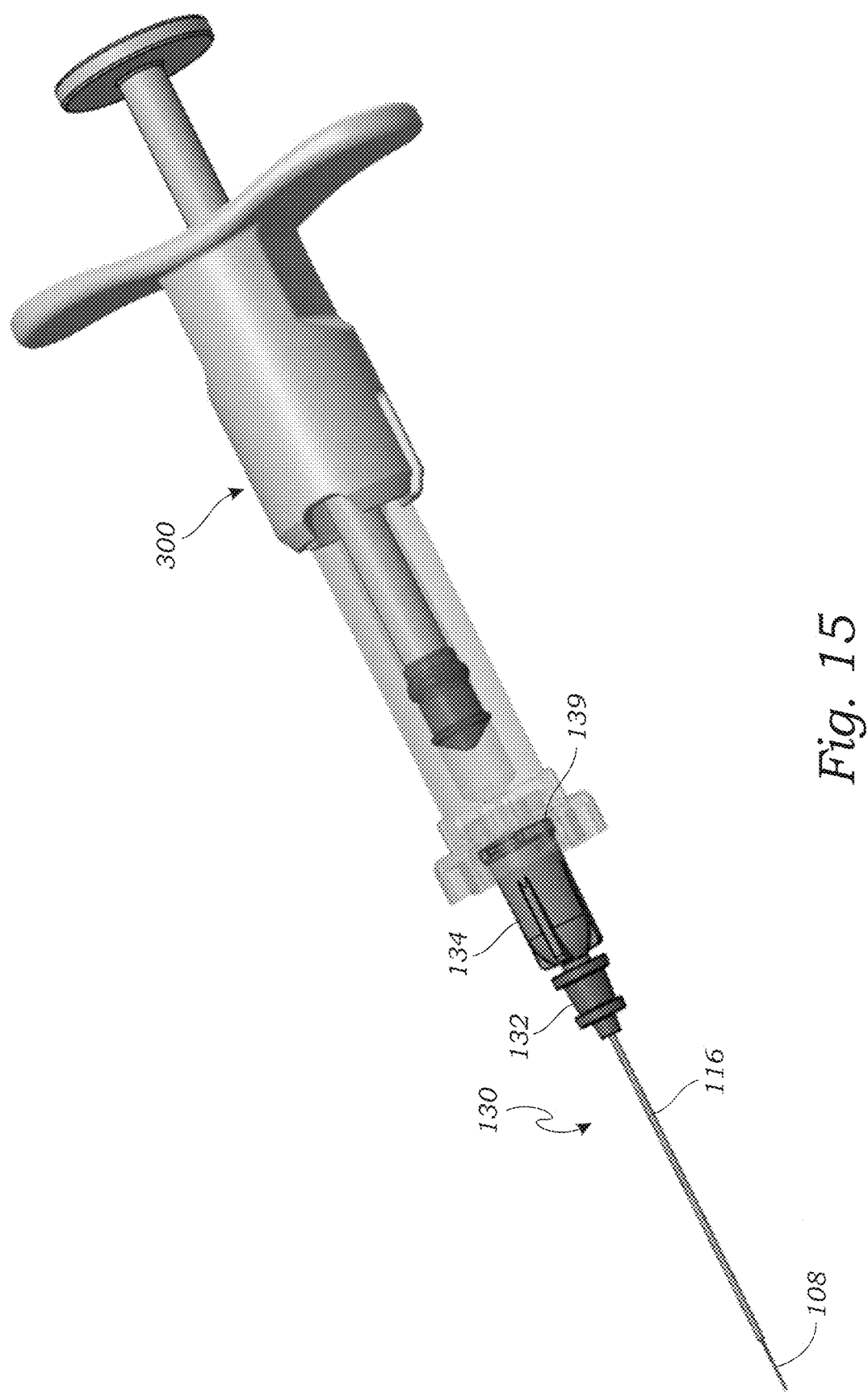
FIG. 15 is a side, perspective view of a syringe connected to the flow cannula illustrated in FIGS. 3A-3H, according to one embodiment.
Figure 16:
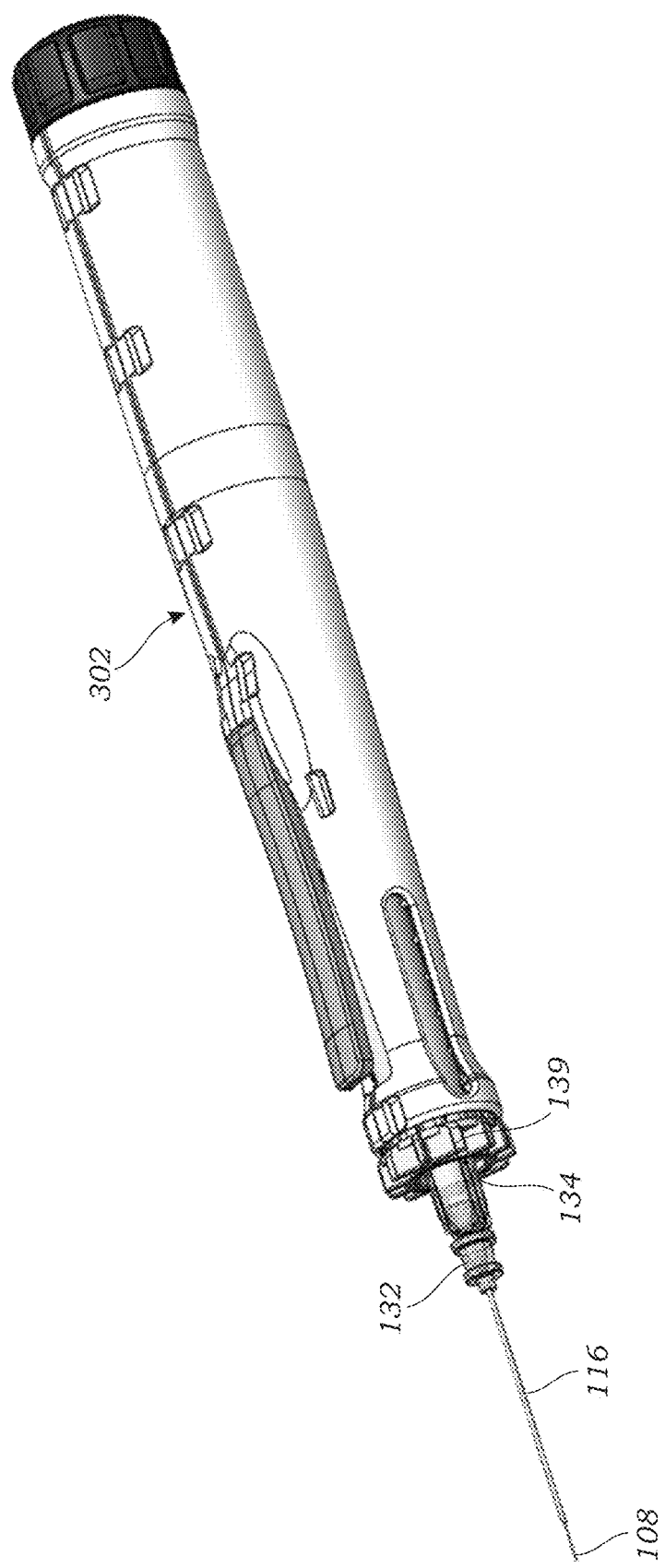
FIG. 16 is a side, perspective view of a self-powered fluid injector connected to the flow cannula illustrated in FIGS. 3A-3H, according to one embodiment.

Turning to FIGS. 2A-2D, a method of using the injector cannula 100 to deliver a medicament into a target site of a patient's body will be described. In the exemplary method shown in FIGS. 2A-2D, the injection is a sub-retinal injection such that the target site is a sub-retinal space 204 beneath the retina 202 of an eye 200. A fluidic injector, such as syringe 300 (see FIG. 15), a self-powered injector 302 (see FIG. 16), or other suitable fluidic injector device, is attached to the proximal end 103 of the flow cannula 102 (e.g., by connecting mating connector on the proximal end 103 of the flow cannula 102 and fluidic injector). As shown in FIG. 2A, a trocar cannula 122 having a trocar valve 124 is inserted into through the outer layers of the eye 200 such that the trocar cannula 122 extends into the vitreous of the eye. The injector cannula 100 is provided with the tip protector tube 116 in the extended position covering and protecting the injector tip 108.

Figure 2B:
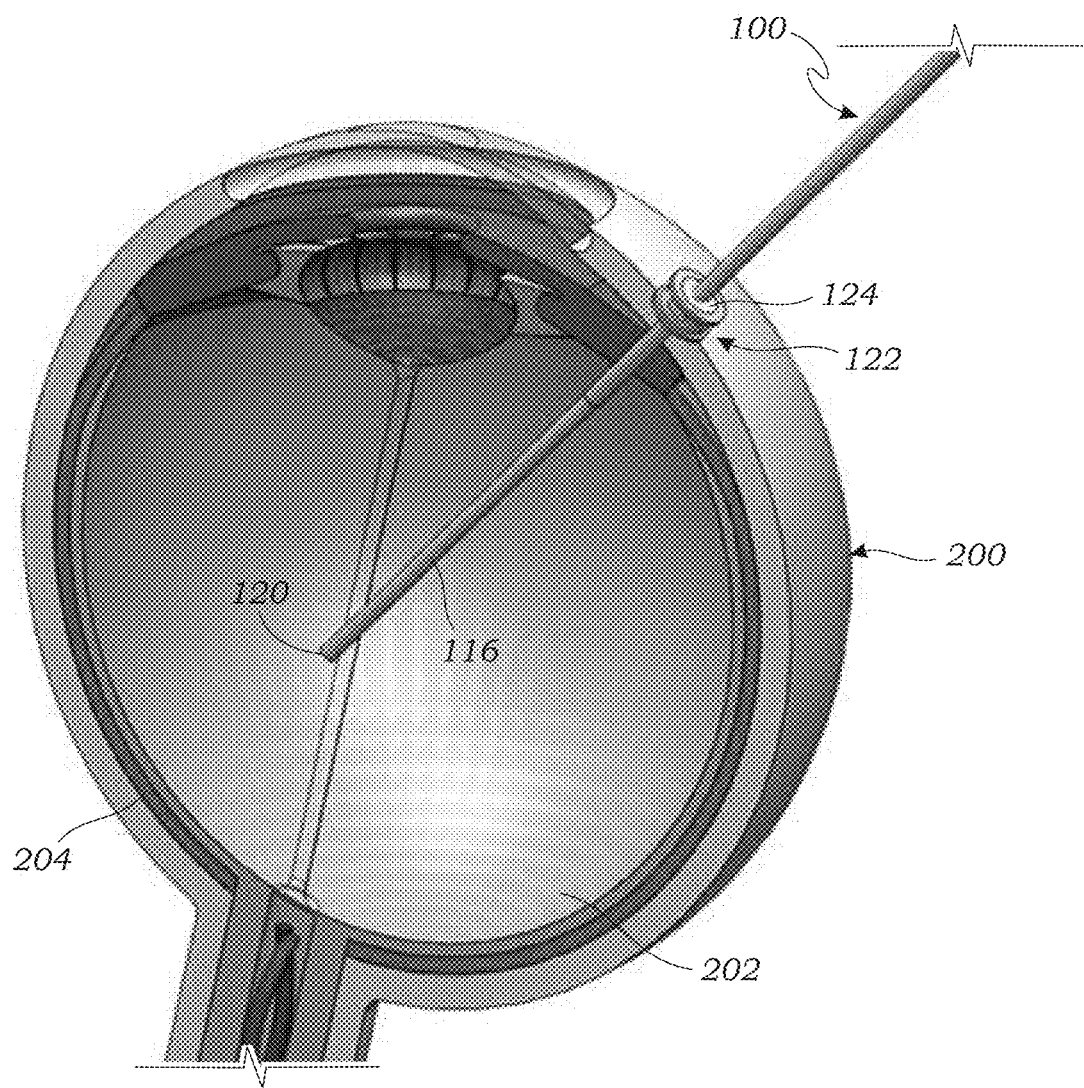
Figure 2C:
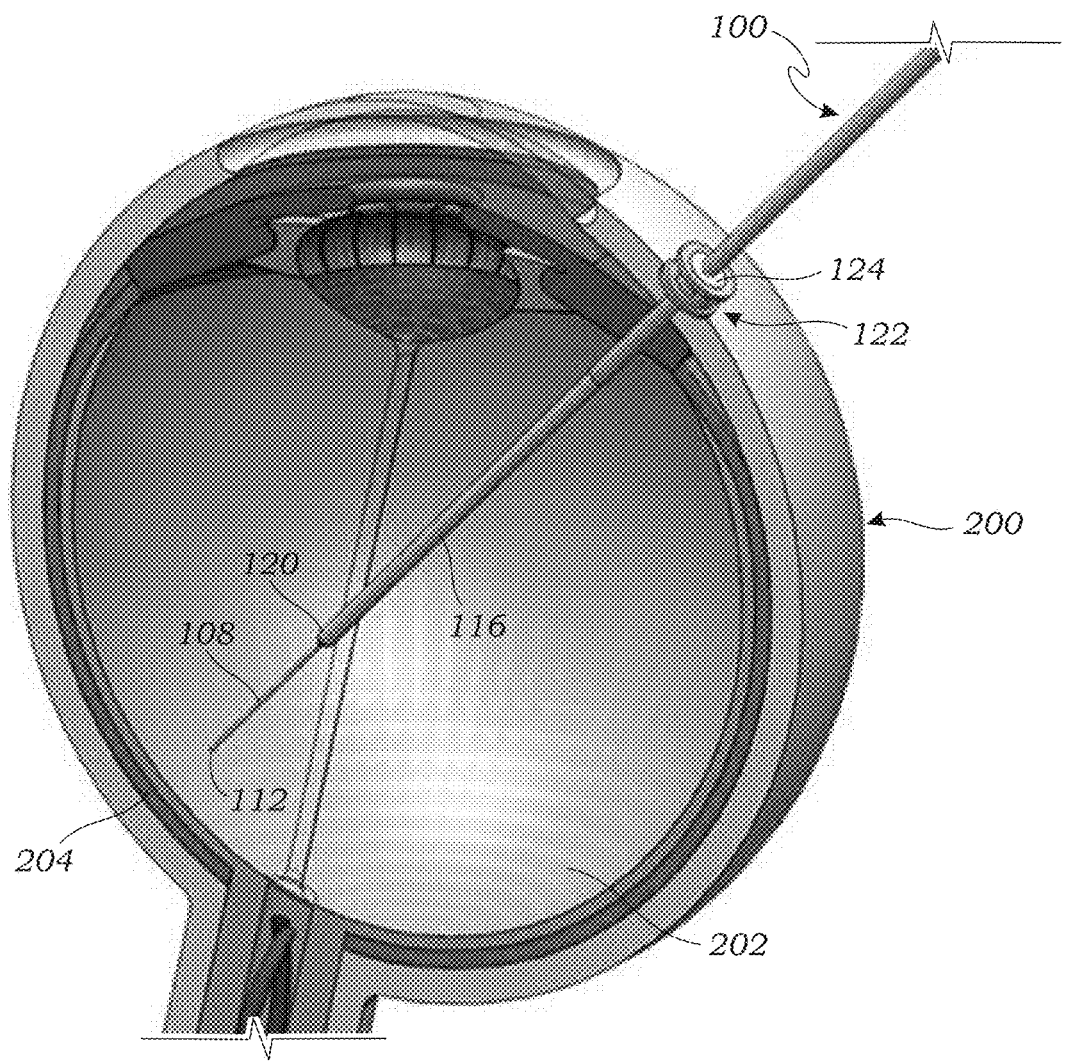

As shown in FIG. 2B, the distal end of the injector cannula 100 (comprising the distal end 120 of the tip protector tube 116) is inserted through the trocar valve 124 and advanced into the vitreous of the eye. The tip protector tube 116 protects the injection tip 108 from being damaged as the injector cannula 100 is advanced through the trocar valve 124. The injector cannula 100 is advanced through the trocar cannula 122 to a desired location. For instance, the injector cannula 100 may be advanced at least to a position in which the full length of the injection tip 108 is safely past (i.e., distal of) the trocar valve 124. Then, as shown in FIG. 2C, the tip protector tube 116 is retracted to the retracted position. This is accomplished by relative movement of the tip protector tube 116 and the flow cannula 102, such that the injection tip 108 is exposed from the tip protector tube 116. As illustrated in FIG. 2C, the tip protector tube 116 is retracted by advancing the flow cannula 102 proximally which positions the tip protector tube 116 in the retracted position thereby exposing the injection tip 108 from the tip protector tube 116. Alternatively, the tip protector tube 116 may be move distally while retaining the flow cannula 102 stationary which positions the tip protector tube 116 in the retracted position thereby exposing the injection tip from the tip protector tube 116. Accordingly, as used herein, the term "retracting the tip protector tube", and similar phrases, means relative movement of the tip protector tube 116 and the flow cannula 102 (or the flow cannula 102 and attached injection tip 108) by moving one or both of the tip protector tube 116 and flow cannula 102.

Figure 2D:
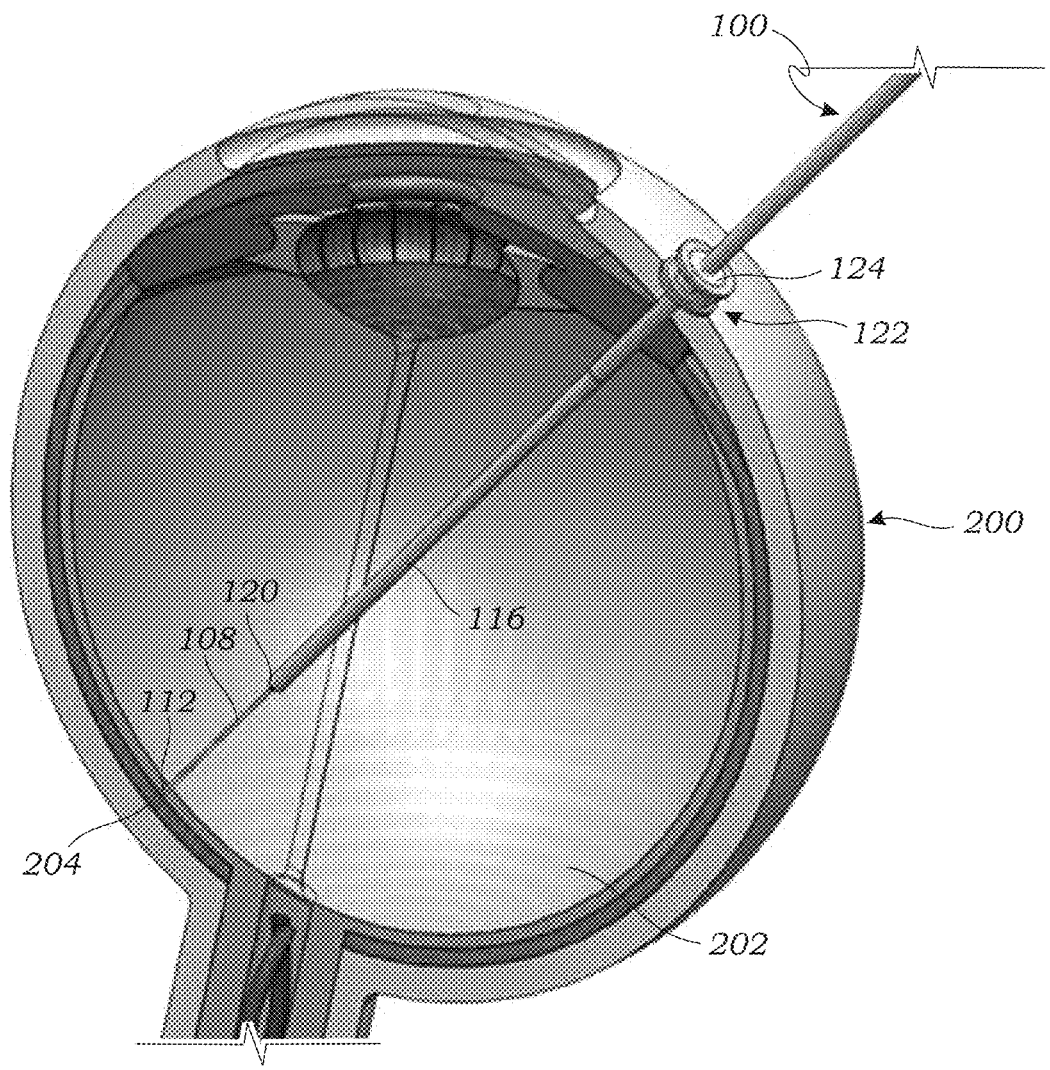

As shown in FIG. 2D, with the tip protector tube 116 in the retracted position, the injector tip 108 is advanced to the target injection site 204, in this example, the sub-retinal space 204. The tip protector tube 116 may pierce body tissue, such as the retina, to position the distal tip 112 at the target injection site 204. The medicament is then injected using the fluidic injector through the flow cannula 102, through the injector tip 108, and into the target injection site 204.

Turning now to FIGS. 3A-3H, another embodiment of an injector cannula 130 is illustrated. The injector cannula 130 is similar to the injector cannula 100, except that the injector cannula 130 also includes a hub 132 and an injector fitting 134. The hub 132 and injector fitting 134 add improved ergonomics and a retention feature for retaining the tip protector tube 116 in the retracted position. The hub 132 is attached to the proximal portion, such as the proximal end 118, of the tip protector tube 116. The hub 132 has is slidably disposed on the flow cannula 102 via a lumen of the hub 132. Accordingly, the hub 132 and tip protector tube 116 are slidable together on the flow cannula 102 from the extended position to the retracted position. The hub 132 has a tapered/conical cavity 136 which is open in the distal direction. An O-ring seal 135 may be disposed on the hub 132 through which the flow cannula 102 passes for providing a friction fit around the flow cannula 102 and prevent backflow or leakage from passing between the flow cannula and the tip protector tube 116. The elastomeric seal may be an O-ring seal, or other suitable seal.

The injector fitting 134 is attached to the proximal portion of the flow cannula 102 such that the injector fitting 134 moves together with the flow cannula 102. The injector fitting 134 has a Luer hub 138 on its proximal end which is configured to be coupled to a fluidic injector having a mating Luer hub, such as syringe 300 (see FIG. 15), a self-powered injector 302 (see FIG. 16), or other suitable fluidic injector device. The injector fitting 134 has tapered/conical protrusion 140 extending from the proximal end of the injector fitting 134. As shown in FIGS. 3E, 3F and 3H, the cavity 136 and conical protrusion 140 are configured to form a taper fit interface (i.e., a retention mechanism) which secures the hub 132 and injector fitting 134 together when they are pressed together upon retracting the hub 132 and tip protector tube 116.

Figure 3D:
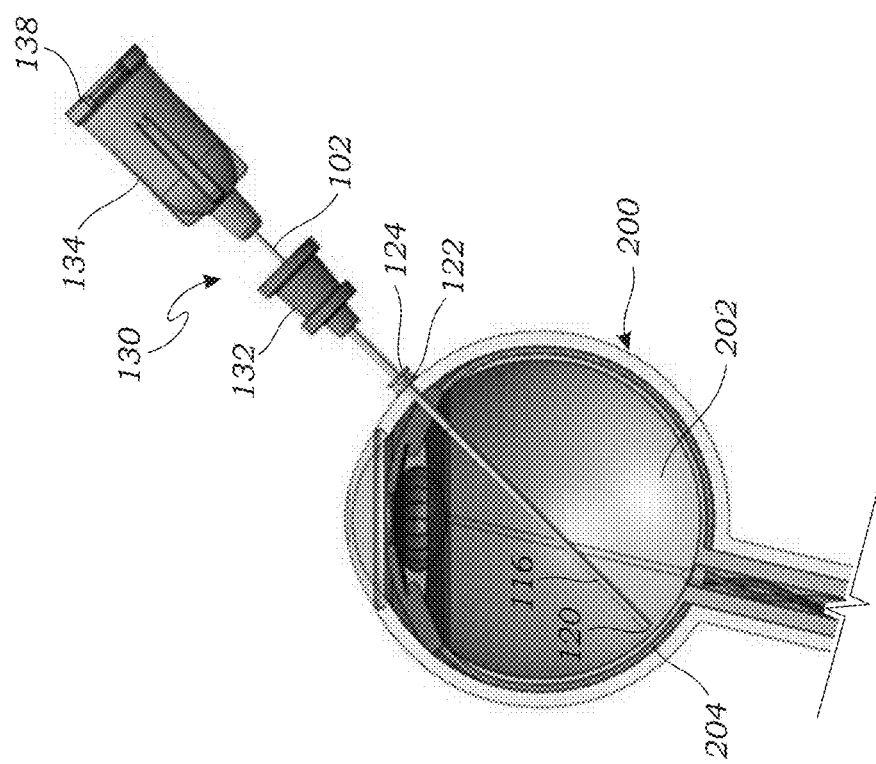
FIG. 3D is side, cut-away view of a human eye illustrating a method of using the injector cannula of FIG. 3A for delivering a medicament into a patient's eye with the tip protector tube in the extended position.
Figure 3A:
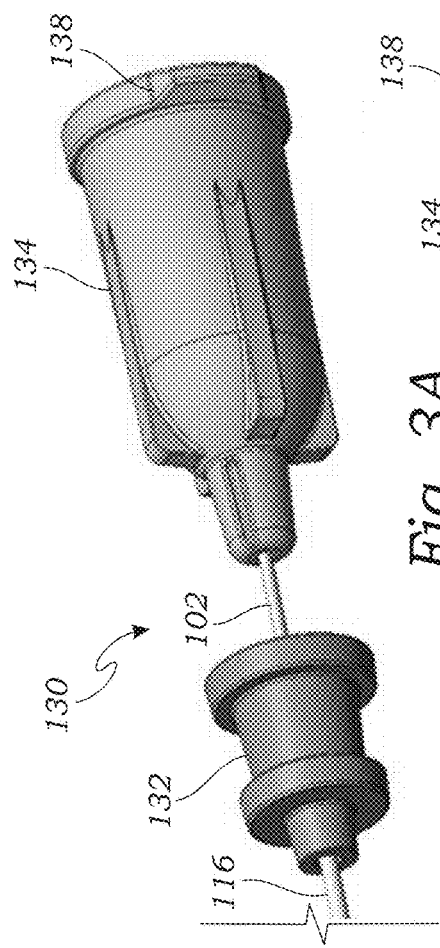
FIG. 3A is a side, perspective view of a proximal portion of an injector cannula having a cooperating hub and Luer fitting retention mechanism, with the tip protector tube in an extended position, according to one embodiment.
Figure 3B:
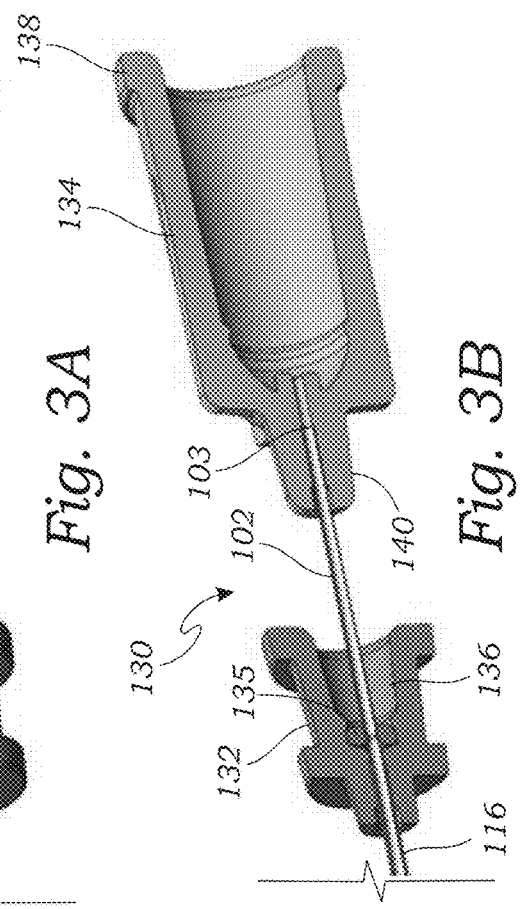
FIG. 3B is a side, cut-away view of the proximal portion of the injector cannula of FIG. 3A with the tip protector tube in an extended position.
Figure 3C:
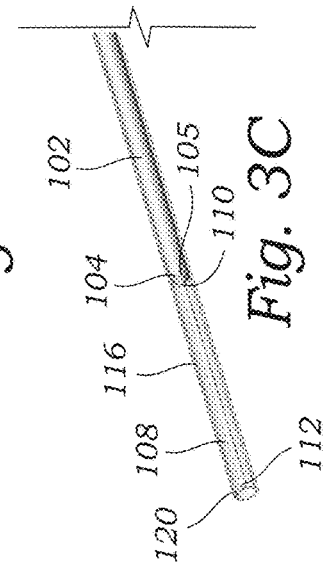
FIG. 3C is a side, perspective view of the distal portion of the injector cannula of FIG. 3A with the tip protector tube in an extended position.

FIG. 3C illustrates the distal portion of the injector cannula 130, which is the same as the injector cannula 100.

Referring to FIGS. 3D and 3H, a method of using the injector cannula 130 to deliver a medicament into a target site of a patient's body is similar to the method of using the injector cannula 110 as described above. A fluidic injector, such as syringe 300 (see FIG. 15), self-powered injector 302 (see FIG. 16), or other suitable fluidic injector device, filled with medicament, is attached to the Luer hub 138 of the injector fitting 134. The fluidic injector has a mating Luer hub 139 which connects to the Luer hub 138 (see FIGS. 15 and 16).

As shown in FIG. 3D, with the hub 132 and tip protector tube 116 in the extended position, the distal end of the injector cannula 130 (comprising the distal end 120 of the tip protector tube 116) is inserted through the trocar valve 124 of the trocar cannula 122 and advanced to a desired location in the vitreous of the eye. The tip protector tube 116 protects the injection tip 108 from being damaged as the injector cannula 130 is advanced through the trocar valve 124.

As shown in FIG. 3H, the hub 132 and tip protector tube 116 are retracted to the retracted position thereby exposing the injector tip 108. FIG. 3H illustrates this being done by moving the hub 132 and tip protector tube 116 distally, while the flow cannula 102 (and attached injection tip 108) is held stationary. The hub 132 and injector fitting 134 provide ergonomic structures for manually retracting the tip protector tube 116 while holding the flow cannula 102 stationary. When the hub 132 and tip protector tube 116 are fully retracted such that the conical protrusion 140 inserts into and is pressed into the conical cavity 136, this interface secures the hub 132 and injector fitting 134 such that the tip protector tube 116 is retained in the retracted position as the injector cannula 130 is moved. The injector cannula 130 may then be operated to inject medicament into the target injection site 204 in the same manner as described for the injector cannula 100.

Turning to FIGS. 4A-4F, another embodiment of an injector cannula 142 is illustrated. The injector cannula 142 is similar to the injector cannula 130, except that the injector cannula 142 has a different design for a hub 144 and an injector fitting 146 which cooperate to provide a retention mechanism which retains the tip protector tube 116 in the extended and retracted positions, and also rotationally aligns, and prevent relative rotation of, the hub 144 to the injector fitting 146. Similar to the injector cannula 130, the hub 144 and injector fitting 146 add improved ergonomics and a retention mechanism for retaining the tip protector tube 116 in the retracted position and also for retaining the tip protector tube in the extended position.

The hub 144 is permanently attached to the proximal portion, such as the proximal end 118, of the tip protector tube 116, e.g., the proximal end 118 may be over-molded or bonded to the hub 144. The hub 144 is slidably disposed on the flow cannula 102 via a lumen of the hub 144. Accordingly, the hub 144 and tip protector tube 116 are slidable together on the flow cannula 102 from the extended position to the retracted position. The hub 144 has one or more pliable snaps or catches 148 extending radially inwardly from a distal portion of the hub 144. The snaps or catches 148 have a slanted proximal side and a substantially straight distal side. The hub 144 may have a plurality of snaps or catches 148 spaced apart circumferentially around the hub, or a single snap or catch 148 which extends around the entire circumference.

The injector fitting 146 is attached to the proximal portion of the flow cannula 102 such that the injector fitting 146 moves together with the flow cannula 102. The injector fitting 146 has a Luer hub 138 on its proximal end which is configured to be coupled to a fluidic injector having a mating Luer hub, such as syringe 300 (see FIG. 15), a self-powered injector 302 (see FIG. 16), or other suitable fluidic injector device. The injector fitting 146 has a protrusion 150 extending from the proximal end of the injector fitting 134. The protrusion 150 has a first notch 152*a* or notches 152*a* at a distal portion of the protrusion 150 and a second notch 152*b* or notches 152*b* at a proximal portion of protrusion 150, such that the first notch(es) 152*a* are spaced apart longitudinally from the second notch(es) 152*b* on the protrusion 150. The notches 152*a* and 152*b* are shaped and configured to separately receive the snaps or catches 148 on the hub 144, such that they cooperate to retain the longitudinal position of the hub 144 relative to the injector fitting 146, which also retains the longitudinal position of the tip protector 116 relative to the flow cannula 102 and the injector tip 108. The first notches 152*a* and second notches 152*b* have a slanted proximal side and a substantially straight distal side. The first notch(es) 152*a* are positioned so that when the snaps or catches 148 are retained in the first notch(es) 152, the hub 144 and tip protector tube 116 are in the extended position, as shown in FIGS. 4A-4C. The second notch(es) 152*b* are positioned so that when the snaps or catches 148 are retained in the second notch(es) 152*b*, the hub 144 and tip protector tube 116 are in the retracted position, as shown in FIGS. 4D-4F. The first notches 152*a* and second notches 152*b* have a slanted proximal side and a substantially straight distal side. The respective substantially straight sides of the snaps or catches 148 and the first notches 152*a* prevent the hub 144 and tip protector tube 116 from being moved distally beyond the extended position. The respective slanted sides of the snaps or catches 148 and the first notches 152 allow the hub 144 to be retracted proximally to the retracted position when a force is in the proximal direction is applied to the hub 144 thereby causing the snaps or catches 148 to flex radially outwardly out of the first notches 152*a*. The respective substantially straight sides of the snaps of catches 148 and the second notches 152*b* prevent the hub 144 and tip protector tube 116 from being moved distally after the hub 144 and tip protector tube 116 are retracted to the retracted position, thereby locking the hub 144 and tip protector tube 116 in the retracted position, as shown in FIGS. 4D-4F.

The hub 144 and injector fitting 146 also have a sliding interface which rotationally aligns the hub 144 relative to the injector fitting 146 and prevents relative rotation of the hub 144 and injector fitting 146. The sliding interface comprises one or more longitudinal slots 154 on the hub 144 and one or more longitudinal ridges or fins 156 on the injector fitting 146 which are received in respective slots 154. In an alternative embodiment, the hub 144 may have ridges or fins which are slidably received in respective slots on the injector fitting 146.

A method of using the injector cannula 142 to deliver a medicament into a target site of a patient's body is substantially the same as the method of using the injector cannula 130 as described above. A fluidic injector, such as syringe 300 (see FIG. 15), self-powered injector 302 (see FIG. 16), or other suitable fluidic injector device, filled with medicament, is attached to the Luer hub 138 of the injector fitting 146 by mating the Luer hub 138 to the Luer hub 139 on the fluidic device. The fluidic injector has a mating Luer hub 139 which connects to the Luer hub 138 (see FIGS. 15 and 16). As shown in FIGS. 4A-4C, with the hub 144 and tip protector tube 116 retained in the extended position by the snaps or catches 148 being received in the first notches 152*a*, the distal end of the injector cannula 142 (comprising the distal end 120 of the tip protector tube 116) is inserted through the trocar valve 124 of the trocar cannula 122 and advanced to a desired location in the vitreous of the eye. The tip protector tube 116 protects the injection tip 108 from being damaged as the injector cannula 142 is advanced through the trocar valve 124.

The hub 144 and tip protector tube 116 are retracted thereby releasing the snaps or catches 148 from the first notches 152*a* and allowing the hub 144 and tip protector tube 116 to be retracted to the retracted position, thereby exposing the injector tip 108, as shown in FIGS. 4D-4F. As the hub 144 and tip protector tube 116 are retracted, the ridges or fins 156 slide in the slots and prevent the hub 144 and tip protector tube 116 from rotating relative to the injector fitting 146 and flow cannula 102. The hub 144 and injector fitting 146 provide ergonomic structures for manually retracting the tip protector tube 116 while holding the flow cannula 102 stationary. As shown in FIGS. 4D-4F, when the hub 132 and tip protector tube 116 are fully retracted, the snaps or catches 148 are received in the second notches 152*b*, thereby retaining and locking the hub 132 and tip protector tube 116 in the retracted position as the injector cannula 142 is moved to position the injector tip at the target injection site. The fluidic injector is then used to inject the medicament through the flow cannula 102, through the injector tip 108, and into the target injection site 204.

Referring now to FIGS. 5A and 5B, another embodiment of an injector cannula 156 which is also similar to the injector cannulas 130 and 142, except that it includes a retraction mechanism for actuating the hub 158 and tip protector tube 116 from the extended position to the retracted position. The injector cannula 156 may have any one or more of the features of the injector cannulas 130 and 142, as describe herein.

The hub 158 is attached to the proximal portion, such as the proximal end 118, of the tip protector tube 116. The hub 158 is slidably disposed on the flow cannula 102 via a lumen of the hub 158. Accordingly, the hub 144 and tip protector tube 116 are slidable together on the flow cannula 102 from the extended position to the retracted position. The hub 158 has a spring flange 164 which provides a bearing surface for a distal side 166 of a retraction spring 162.

The injector fitting 160 is attached to the proximal portion of the flow cannula 102 such that the injector fitting 160 moves together with the flow cannula 102. The injector fitting 160 may have a Luer hub (not shown) on its proximal end which is configured to be coupled to a fluidic injector having a mating Luer hub, such as syringe 300 (see FIG. 15), a self-powered injector 302 (see FIG. 16), or other suitable fluidic injector device. The injector fitting 160 has a protrusion 165 which extends into the hub 158. The protrusion 165 has a spring support 168 which provides a bearing surface for a proximal side of the retraction spring 162.

The retraction spring 162 is in compression such that it biases the hub 158 and tip protector tube 116 toward the retracted position.

The injector cannula 156 has a bayonet interface/fitting 170 between the hub 158 and the injector fitting 160 which functions as a retention/release mechanism. In a locked position, the bayonet interface 170 retains the hub 158 and tip protector tube 116 in the extended position and upon actuation to a release position, the bayonet interface 170 release the hub 158 allowing the retraction spring 162 to force the hub 158 to the retracted position. The injector cannula 156 may utilized other retention/release mechanisms, such as a push-button latch release, or a detent position actuatable by an axial force, or other suitable mechanism.

The configurations of the flow cannula 102, injector tip 108, and tip protector tube 116 are the same or similar to the injector cannulas 130 and 142.

A method of using the injector cannula 156 to deliver a medicament into a target site of a patient's body is substantially the same as the method of using the injector cannulas 130 and 142, as described above. A fluidic injector, such as syringe 300 (see FIG. 15), self-powered injector 302 (see FIG. 16), or other suitable fluidic injector device, filled with medicament, is attached to the Luer hub 138 of the injector fitting 160 by mating the Luer hub 138 to the Luer hub 139 on the fluidic device.

With the hub 158 and tip protector tube 116 retained in the extended position by the bayonet interface 170 in its locked position, the distal end of the injector cannula 142 (comprising the distal end 120 of the tip protector tube 116) is inserted through the trocar valve 124 of the trocar cannula 122 and advanced to a desired location in the vitreous of the eye. The tip protector tube 116 protects the injection tip 108 from being damaged as the injector cannula 156 is advanced through the trocar valve 124.

The bayonet interface 170 is then actuated to the release position, which allows the retraction spring 162 to retract the hub 158 and tip protector tube 116 to the retracted position, thereby exposing the injector tip 108. The injector cannula 130 is moved to position the injector tip 108 at the target injection site. The fluidic injector is then used to inject the medicament through the flow cannula 102, through the injector tip 108, and into the target injection site 204.

Turning to FIGS. 6A-6D, another embodiment of an injector cannula 172 is illustrated. The injector cannula 172 is similar to the injector cannula 142, except that the injector cannula 172 has a different design for a hub 174 and an injector fitting 176. The hub 174 and injector fitting 176 are configured to cooperate to provide a retention mechanism which retains the tip protector tube 116 in the extended and retracted positions, and also to rotate the hub 174 relative to the injector fitting as the hub 174 is retracted from the extended position to the retracted position. Similar to the injector cannula 142, the hub 174 and injector fitting 176 add improved ergonomics and a retention mechanism for retaining the tip protector tube 116 in the retracted position and the extended position.

The hub 174 is attached to the proximal portion, such as the proximal end 118, of the tip protector tube 116. The hub 174 is slidably disposed on the flow cannula 102 via a lumen of the hub 174. Accordingly, the hub 174 and tip protector tube 116 are slidable together on the flow cannula 102 from the extended position to the retracted position. The hub 174 has cylindrical cavity and a raised feature, such as a bump 180 on the inside surface of hub extending into the cavity. The raised bump 180 is positioned on the proximal portion of the hub 174.

Figure 6A:
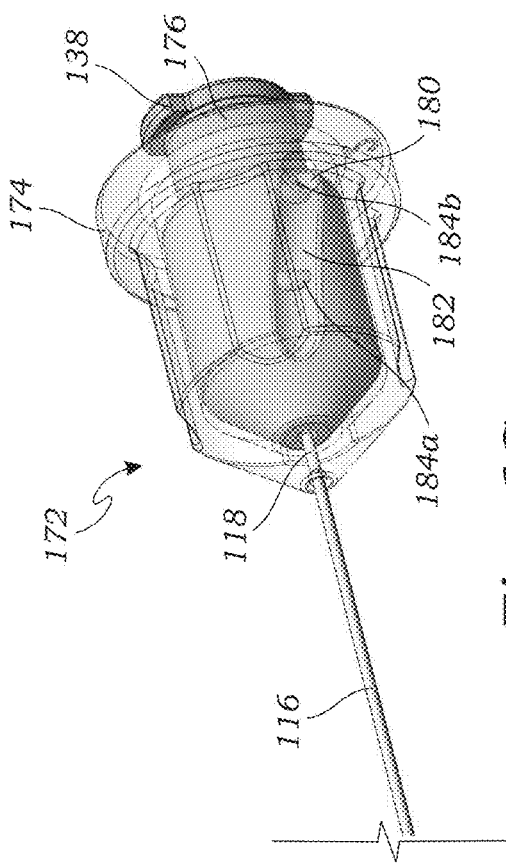
FIG. 6A is a side, perspective view of a proximal portion of an injector cannula having a cooperating hub and Luer fitting retention mechanism, with the tip protector tube in an extended position, according to another embodiment.
Figure 6B:
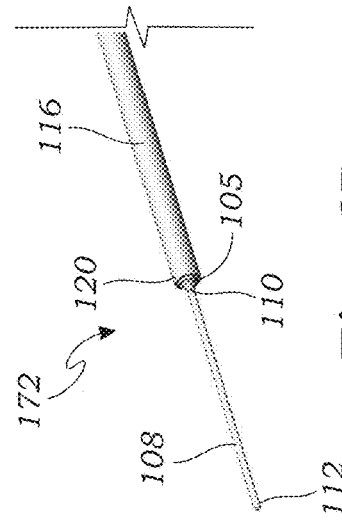
FIG. 6B is a side, perspective view of the distal portion of the injector cannula of FIG. 6A with the tip protector tube in an extended position.
Figure 6C:
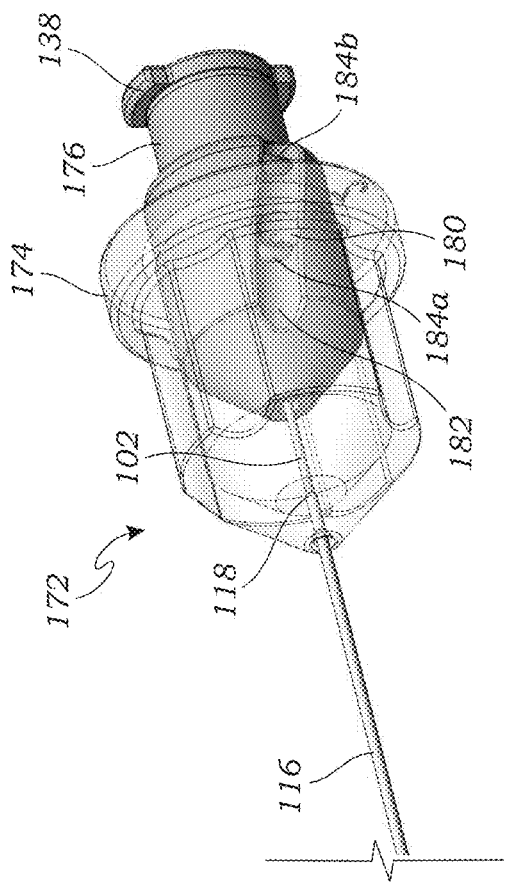
FIG. 6C is a side, perspective view of a proximal portion of an injector cannula of FIG. 4A, with the tip protector tube in a retracted position, according to one embodiment.
Figure 6D:
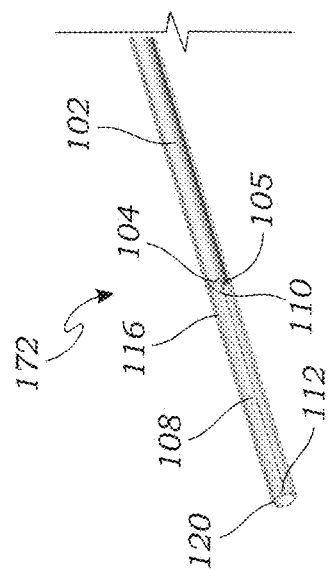
FIG. 6D is a side, perspective view of the distal portion of the injector cannula of FIG. 6A with the tip protector tube in the retracted position.

The injector fitting 176 is attached to the proximal portion of the flow cannula 102 such that the injector fitting 176 moves together with the flow cannula 102. The injector fitting 176 has a Luer hub 138 on its proximal end which is configured to be coupled to a fluidic injector having a mating Luer hub, such as syringe 300 (see FIG. 15), a self-powered injector 302 (see FIG. 16), or other suitable fluidic injector device. The injector fitting 176 has a cylindrical body which fits into the cylindrical cavity of the hub 174. The cylindrical body has a groove 182 in the outside surface of the cylindrical body. The groove 182 is shaped and configured to receive the raised bump 180 on the hub 174. The groove 180 extends along a helical path. There is a first detent 184a in the groove 182 configured to receive the raised bump 180. The first detent 184a is positioned so that when the raised bump 180 is received in the first detent 184a, the hub 174 and tip protector tube 116 are retained in the extended position, as shown in FIGS. 6A-6C. The injector fitting 176 has a second detent 184b in the groove 182 configured to receive the raised bump 180, and positioned so that when the raised bump 180 is received in the second detent 184b, the hub 174 and tip protector tube 116 are retained in the retracted position, as shown in FIGS. 6A-6C. Accordingly, the first detent 184a is spaced apart longitudinally from the second detent 184b. The raised bump 180 and the first detent 184a are configured such that when a sufficient force is applied to the hub 174 in the proximal direction, the raised bump 180 releases from the first detent 184a thereby allowing the hub 174 and tip protector tube 116 to be retracted to the retracted position. The helical path of the groove 182 causes the hub 174 to rotate about its longitudinal axis as it is moved longitudinally, such as when it is retracted to the retracted position, as the raised bump 180 follows the groove 182.

In alternative embodiments, the groove 180 may have a linear path along parallel to the longitudinal axis, or a hook shape to provide a bayonet type retention mechanism, or other suitable geometry.

A method of using the injector cannula 172 to deliver a medicament into a target site of a patient's body is substantially the same as the method of using the injector cannulas 130 and 142, as described above. A fluidic injector, such as syringe 300 (see FIG. 15), self-powered injector 302 (see FIG. 16), or other suitable fluidic injector device, filled with medicament, is attached to the Luer hub 138 of the injector fitting 176 by mating the Luer hub 138 to the Luer hub 139 on the fluidic device. With the hub 174 and tip protector tube 116 retained in the extended position by raised bump 180 being received in the first detent 184a, the distal end of the injector cannula 142 (comprising the distal end 120 of the tip protector tube 116) is inserted through the trocar valve 124 of the trocar cannula 122 and advanced to a desired location in the vitreous of the eye. The tip protector tube 116 protects the injection tip 108 from being damaged as the injector cannula 142 is advanced through the trocar valve 124.

The hub 174 and tip protector tube 116 are retracted thereby releasing the raised bump 180 from the first detent 184a and allowing the hub 174 and tip protector tube 116 to be retracted to the retracted position, thereby exposing the injector tip 108. As the hub 174 and tip protector tube 116 are retracted, the raised bump 180 follows the helical path of the groove 182 thereby causing the hub 174 and tip protector tube 116 to rotate relative to the injector fitting 176 and flow cannula 102. When the hub 174 and tip protector tube 116 are fully retracted, the raise bump 180 is received in the second detent 184b, thereby retaining the hub 174 and tip protector tube 116 in the retracted position as the injector cannula 172 is moved to position the injector tip 108 at the target injection site. The fluidic injector is then used to inject the medicament through the flow cannula 102, through the injector tip 108, and into the target injection site 204.

Turning to FIGS. 7A-7E, another embodiment of an injector cannula 186 is illustrated. The injector cannula 186 is similar to the injector cannula 172, except that the injector cannula 186 has a different design for a hub 188 and an injector fitting 190. Like injector cannula 172, the hub 188 and injector fitting 190 of injector cannula 186 are configured to cooperate to provide a retention mechanism which retains the tip protector tube 116 in the extended and retracted positions, and also to rotationally align, and prevent relative rotation of, the hub 188 and the injector fitting 190. Similar to the injector cannula 172, the hub 188 and injector fitting 190 add improved ergonomics and a retention mechanism for retaining the tip protector tube 116 in the retracted position and the extended position.

The hub 188 is attached to the proximal portion, such as the proximal end 118, of the tip protector tube 116. The hub 188 is slidably disposed on the flow cannula 102 via a lumen of the hub 188. Accordingly, the hub 188 and tip protector tube 116 are slidable together on the flow cannula 102 from the extended position to the retracted position. The hub 188 has cylindrical cavity and a plurality of longitudinal grooves 192 spaced apart circumferentially and extending into the cavity. The exemplary embodiment of FIGS. 7A-7E has four grooves 192 spaced at 90°. There is a raised feature, such as a raised bump 194, in each of the grooves 192 at a proximal end of each groove.

The injector fitting 190 is attached to the proximal portion of the flow cannula 102 such that the injector fitting 190 moves together with the flow cannula 102. The injector fitting 190 has a Luer hub 138 on its proximal end which is configured to be coupled to a fluidic injector having a mating Luer hub, such as syringe 300 (see FIG. 15), a self-powered injector 302 (see FIG. 16), or other suitable fluidic injector device. The injector fitting 190 has a cylindrical body which fits into the cylindrical cavity of the hub 188. The cylindrical body has a plurality of raised fins 196 slidably received in a respective groove 192 of the hub 188. Each of the raised fins 196 has a first detent 198a (such as a notch) configured to receive a respective raised bump 194. The first detent 198a is positioned so that when the raised bump 180 is received in the first detent 198a, the hub 188 and tip protector tube 116 are retained in the extended position, as shown in FIGS. 7A-7C. Each of the raised fins 196 also has a second detent 198b configured to receive a respective raised bump 194, and positioned so that when the raised bump 194 is received in the second detent 198b, the hub 188 and tip protector tube 116 are retained in the retracted position, as shown in FIGS. 7D-7E. Accordingly, the first detent 198a is spaced apart longitudinally from the second detent 198b. The raised bumps 194 and the respective first detents 198a are configured such that when a sufficient force is applied to the hub 188 in the proximal direction, the raised bumps 194 release from the respective first detents 198a thereby allowing the hub 188 and tip protector tube 116 to be retracted to the retracted position. The raised fins 196 slidably received in the respective grooves 192 rotationally align the hub 188 and the injector fitting 190 and also and prevent relative rotation of the hub 188 and injector fitting 190.

A method of using the injector cannula 186 to deliver a medicament into a target site of a patient's body is substantially the same as the method of using the injector cannulas 142 and 172 as described above. A fluidic injector, such as syringe 300 (see FIG. 15), self-powered injector 302 (see FIG. 16), or other suitable fluidic injector device, filled with medicament, is attached to the Luer hub 138 of the injector fitting 190 by mating the Luer hub 138 to the Luer hub 139 on the fluidic device.

With the hub 188 and tip protector tube 116 retained in the extended position by raised bumps 194 being received in the respective first detents 198a, the distal end of the injector cannula 172 (comprising the distal end 120 of the tip protector tube 116) is inserted through the trocar valve 124 of the trocar cannula 122 and advanced to a desired location in the vitreous of the eye. The tip protector tube 116 protects the injection tip 108 from being damaged as the injector cannula 142 is advanced through the trocar valve 124.

The hub 188 and tip protector tube 116 are retracted thereby releasing the raised bumps 194 from the respective first detents 198a and allowing the hub 188 and tip protector tube 116 to be retracted to the retracted position, thereby exposing the injector tip 108. As the hub 188 and tip protector tube 116 are retracted, the raised fins 196 slidably received in the respective grooves prevent relative rotation of the hub 188 and injector fitting 190.

When the hub 188 and tip protector tube 116 are fully retracted, the raised bumps 194 are received in the respective second detents 198b, thereby retaining the hub 188 and tip protector tube 116 in the retracted position as the injector cannula 186 is moved to position the injector tip 108 at the target injection site. The fluidic injector is then used to inject the medicament through the flow cannula 102, through the injector tip 108, and into the target injection site 204.

Figure 12:
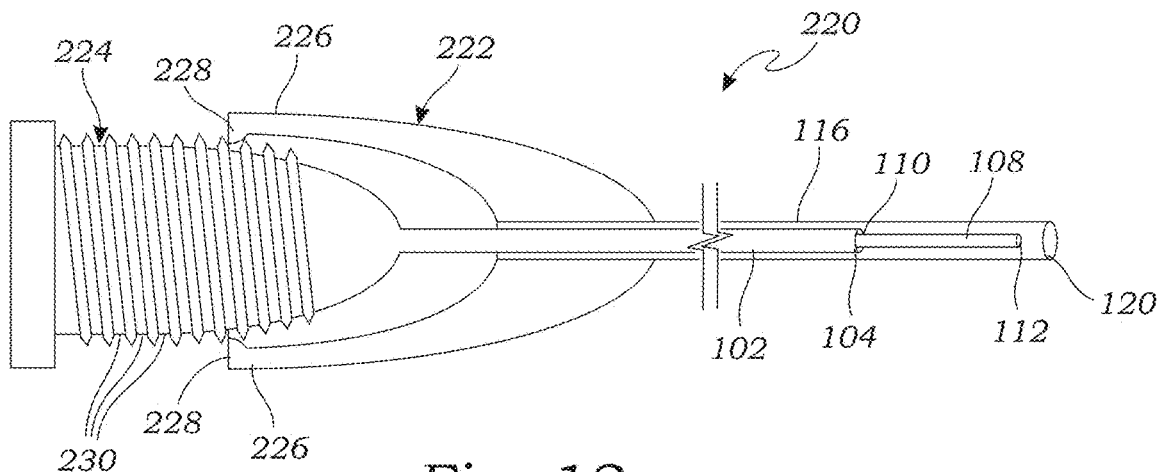
FIG. 12 is a side, partial cross-sectional view of a proximal portion of still another injector cannula having a cooperating hub and Luer fitting retention mechanism, according to another embodiment.

Turning to FIG. 12, another embodiment of an injection cannula 220 having another design for a hub 222 and an injector fitting 224 (which together form a retention/retraction mechanism) is illustrated. The injector cannula 220 is similar to the injector cannulas 172 and 186, except that the injector cannula 220 has a different design for a hub 222 and an injector fitting 224. Like injector cannulas 172 and 186, the hub 222 and injector fitting 224 of injector cannula 220 are configured to cooperate to provide a retention mechanism which retains the tip protector tube 116 in the extended and retracted positions. The hub 222 is coupled to the tip protector tube 116, and the injector fitting 224 is coupled to the flow cannula 102 same or similar to the injector cannulas 172 and 186.

The hub 222 includes a plurality of retention arms 226. A respective retention catch 228 is disposed on a proximal end of each retention arm 226. The injector fitting 224 has a plurality of circumferential ratchet grooves 230 spaced apart longitudinally on the injector fitting 224. The ratchet grooves 224 and retention catches 228 interface with each other to retain the hub 222 and tip protector tube 116 in a plurality of different longitudinally spaced apart positions, including the extended position and the retracted position.

A method of using the injection cannula 220 to deliver a medicament into a target site of a patient's body is substantially the same as the method of using the injector cannulas 172 and 186, as described above.

Figure 13:
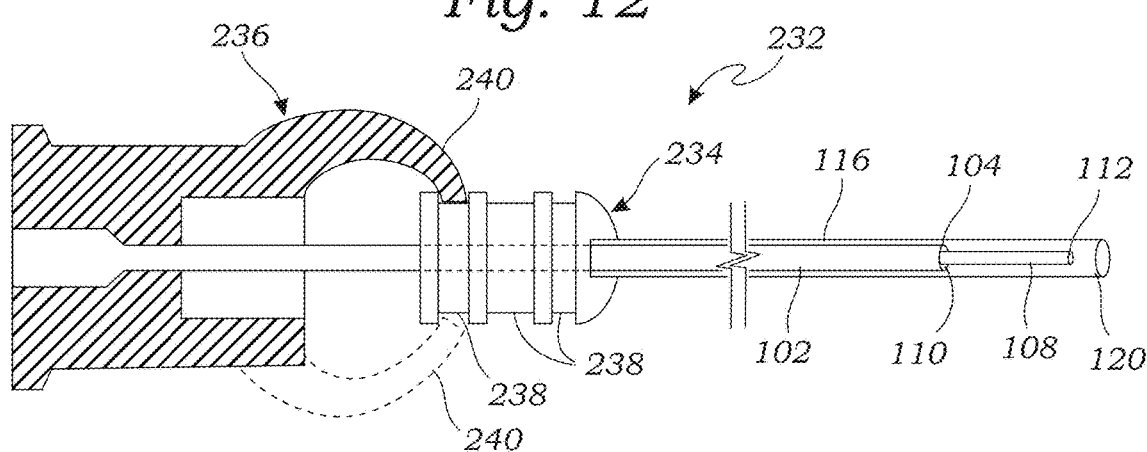
FIG. 13 is a side partial cross-sectional view of a proximal portion of yet another injector cannula having a cooperating hub and Luer fitting retention mechanism, according to another embodiment.

Turning to FIG. 13, still another embodiment of an injection cannula 232 having another design for a hub 234 and an injector fitting 236 (which together form a retention/retraction mechanism) is illustrated. The injector cannula 232 is similar to the injector cannula 172, 186 and 220, except that the injector cannula 220 has a different design for a hub 234 and an injector fitting 236. Like injector cannulas 172, 186 and 220, the hub 234 and injector fitting 236 of injector cannula 232 are configured to cooperate to provide a retention mechanism which retains the tip protector tube 116 in the extended and retracted positions. The hub 234 is coupled to the tip protector tube 116, and the injector fitting 236 is coupled to the flow cannula 102 same or similar to the injector cannulas 172 and 186.

The hub 234 includes a plurality of circumferential ratchet grooves 238 spaced apart longitudinally on the hub 234. The injector fitting 236 has a plurality of retention arms 240. The ratchet grooves 238 and retention arms 240 interface with each other to retain the hub 234 and tip protector tube 116 in a plurality of different longitudinally spaced apart positions, including the extended position and the retracted position.

A method of using the injection cannula 232 to deliver a medicament into a target site of a patient's body is substantially the same as the method of using the injector cannulas 172, 186 and 220, as described above.

Figure 14A:
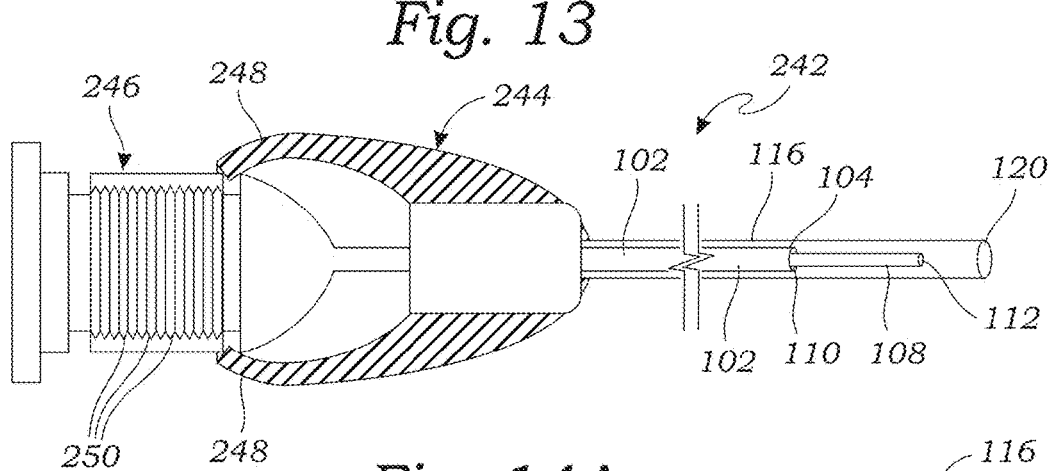
FIG. 14A is a side partial cross-sectional view of a proximal portion of yet another injector cannula having a cooperating hub and Luer fitting retention mechanism, according to another embodiment.
Figure 14B:
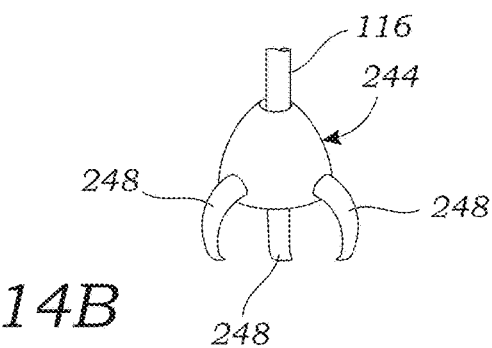
FIG. 14B is a perspective view of the hub portion of the injector cannula of FIG. 14A.

Turning to FIGS. 14A and 14B, another embodiment of an injection cannula 242 having another design for a hub 244 and an injector fitting 246 (which together form a retention/retraction mechanism) is illustrated. The injector cannula 242 is similar to the injector cannulas 172, 186, 220 and 232, except that the injector cannula 242 has a different design for a hub 244 and an injector fitting 246. Like injector cannulas 172, 186, 220 and 232, the hub 244 and injector fitting 246 of injector cannula 242 are configured to cooperate to provide a retention mechanism which retains the tip protector tube 116 in the extended and retracted positions. The hub 244 is coupled to the tip protector tube 116, and the injector fitting 246 is coupled to the flow cannula 102 same or similar to the injector cannulas 172, 186, 220 and 232.

The hub 244 includes a plurality of retention arms 248. The injector fitting 246 has a plurality of circumferential ratchet grooves 250 spaced apart longitudinally on the injector fitting 246. The ratchet grooves 250 and retention arms 248 interface with each other to retain the hub 244 and tip protector tube 116 in a plurality of different longitudinally spaced apart positions, including the extended position and the retracted position.

A method of using the injection cannula 242 to deliver a medicament into a target site of a patient's body is substantially the same as the method of using the injector cannulas 172, 186, 22 and 232, as described above.

Figure 8A:
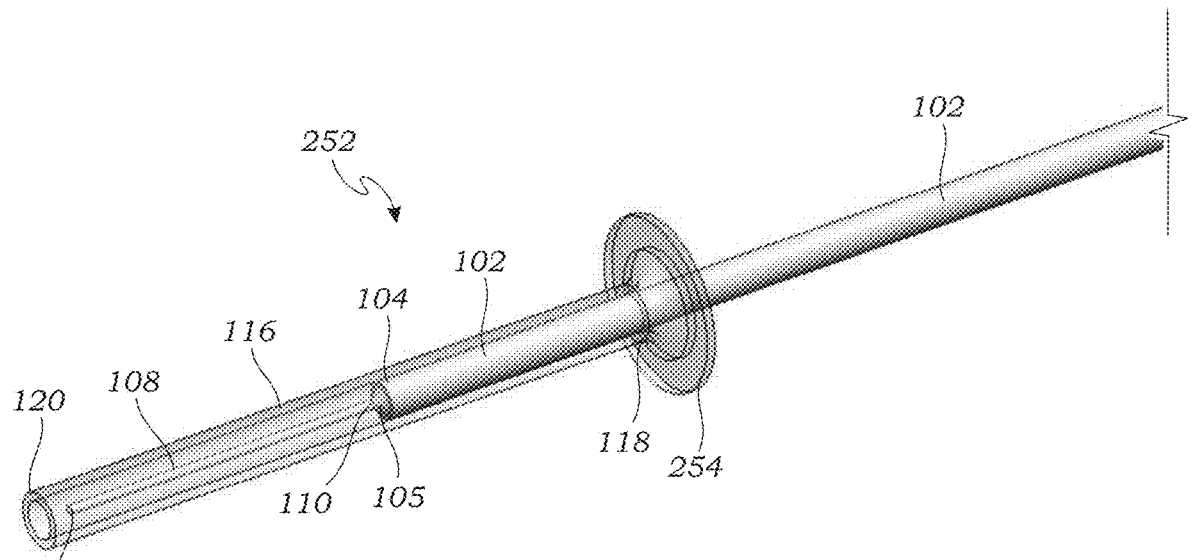
FIG. 8A is a side, perspective view of a distal portion of an injector cannula having a shortened tip protector tube in an extended position, according to one embodiment.
Figure 8B:
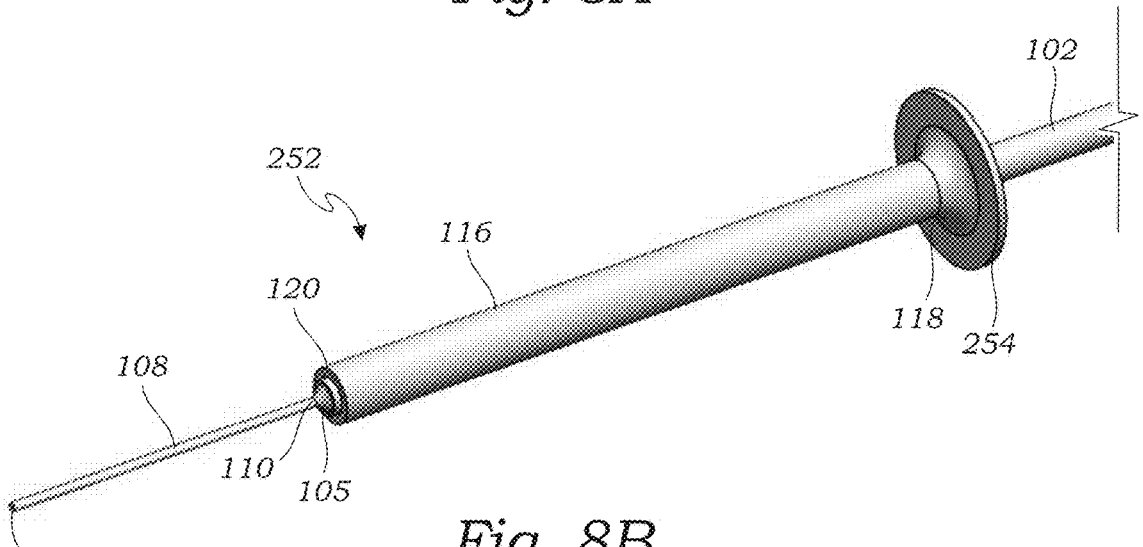
FIG. 8B is a side, perspective view of the distal portion of the injector cannula of FIG. 8A with the tip protector tube retracted to a retracted position, according to one embodiment.

Referring to FIGS. 8A-8B, another embodiment of an injector cannula 252 for delivering a medicament into a patient's body is illustrated. This injector cannula is similar to the injector cannulas 100 and 130, except that it utilizes a shorter tip protector tube 116 which does not extend proximally to the injector fitting 134 in the fully retracted position. The tip protector tube 116 includes a tip protector tube stop 120 or 254 which is configured to contact a hard stop 121 or 124 on the trocar cannula 122 as the injector cannula 252 is advanced through the trocar cannula 122. The cooperating stops 120/121 or 254/124 also retract the tip protector tube 116 from the extended position to the retracted position as the flow cannula 102 and injection tip 108 are advanced after the tip protector tube 116 is stopped by the cooperating stops 120/121 or 254/124.

The injector cannula 252 includes a flow cannula 102 having a proximal end 103 (see e.g., FIG. 3B) and a distal end 104 defining a flow cannula length from the proximal end 103 to the distal end 104. An injector fitting 134 is attached to the proximal portion of the flow cannula 102 (see FIG. 11D). The injector fitting 134 may be the same or similar to the injector fitting 134 on the injector cannula 130. A flexible injector tip 108 is attached to the distal end 104 of the flow cannula 102 and extends distally from the flow cannula 102. The injector tip 108 has a proximal end 110 and a distal end 112 defining a full length of the injector tip 108.

A tip protector tube 116 is slidably disposed on the flow cannula 102. The tip protector tube 116 has a proximal end 118 and a distal end 120 defining a tip protector tube length. The tip protector tube 116 is slidable on the flow cannula 102 from an extended position in which the tip protector tube 116 covers the entire injector tip 108, a retracted position in which the tip protector tube 116 is retracted proximally thereby exposing at least part of the injector tip, and a fully retracted position in which the distal end 120 of the tip protector tube 116 is aligned with, or proximal of (e.g., up to 0.1 mm proximal of), the proximal end 110 of the injector tip 108 such that the full length of the injector tip 108 is exposed from the tip protector tube 116. The tip protector tube length is configured such that in the fully retracted position the proximal end 118 of the tip protector tube 116 is located proximal of the injector fitting 134. The tip protector tube 116 is substantially stiffer than the injector tip 108. For example, the tip protector tube 116 has sufficient stiffness that it can be pushed through the valve 124 of a trocar valve 122 without bending or crushing such that it protects the injector tip 102 from being damaged.

The injector cannula 252 is configured such that tip protector tube 116 can be shorter than the tip protector tube 116 of the injector cannulas 100 and 130, because the tip protector tube 116 does not need to extend proximally to the injector fitting 134, and the tip protector tube 116 is not advanced completely when advancing the flow cannula 102 and injector tip 108 all the way to the target injection site, as explained herein. In other words, the tip protector tube 116 is advanced sufficiently through the trocar valve 124 to protect the delicate injection tip 108 as it is advanced through the trocar valve 124, and then the tip protector tube 116 is stopped. For example, the tip protector tube length may be less than one half the flow cannula length, or less than 75% of the flow cannula length. Alternatively, the tip protector tube length may be less than 150% of the full length of the injector tip 108.

A handle 254, which may also function as a protector tube stop 254, is attached to the proximal end 118 of the tip protector tube 116. The handle 254 shown in the illustrated embodiment comprises a flared portion of a proximal portion of the tip protector tube 116. In alternative embodiments, the handle 254 may be a separate handle component attached to the proximal end 118 of the tip protector tube 116.

Figure 9A:
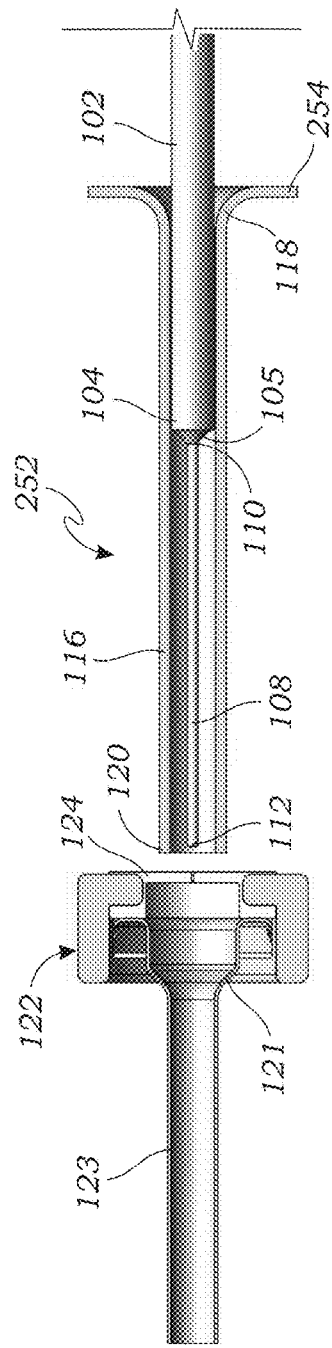
FIGS. 9A-9C are side, partial cross-sectional views of the injector cannula of FIG. 8A illustrating one method of operation, according to one embodiment.
Figure 9B:
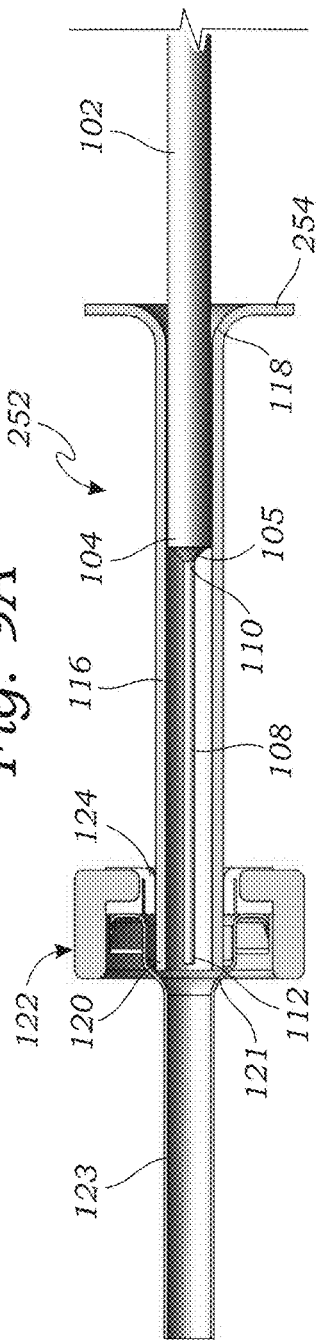
Figure 9C:
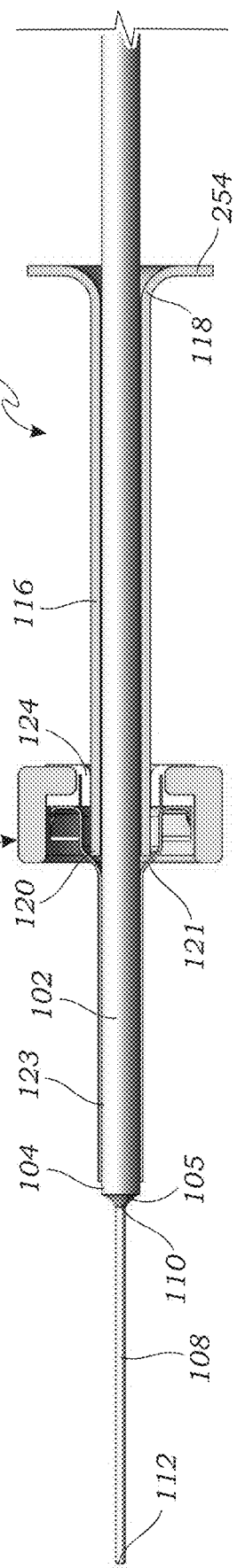

As illustrated in FIGS. 9A-9C, the distal end 120 of the tip protector tube 116 may be configured to contact a hard stop 121 (e.g., a proximal end of a trocar tube 123 of the trocar cannula 122) of the trocar cannula 122 to prevent further advancement of the tip protector tube 116 into the trocar cannula 122. FIG. 9A shows the injector cannula 252 with the tip protector tube 116 in the extended position. FIG. 9B shows the distal end of the injector cannula 252 (comprising the distal end of 120 of the tip protector tube 116) with the tip protector tube 116 in the extended position being advanced through the trocar valve 124. The tip protector tube 116 protects the injector tip 108 from being damaged as the injector cannula 252 is advance through the trocar valve 124. FIG. 9B also shows the injector cannula 252 as the tip protector tube stop 120 (comprising the distal end 120 of the tip protector tube 116) contacting the hard stop 121 (comprising a proximal end of a trocar tube 123 of the trocar cannula 122). FIG. 9C illustrates the tip protector tube 116 being retracted to the retracted to the retracted position by further advancing the flow cannula 102 and injector tip 108 while the tip protector tube 116 is stopped from further advancement by the cooperating stops 120/121.

Figure 10A:
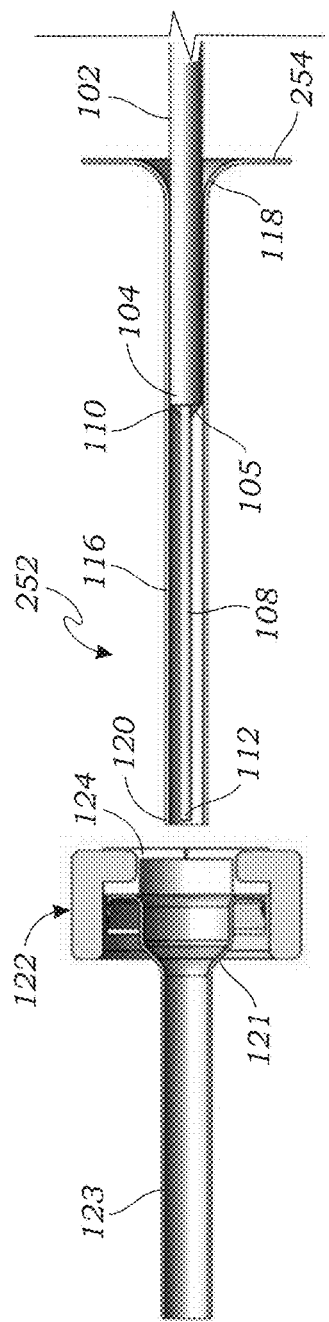
FIGS. 10A-10C are side, partial cross-sectional views of the injector cannula of FIG. 8A illustrating another method of operation, according to another embodiment.
Figure 10B:
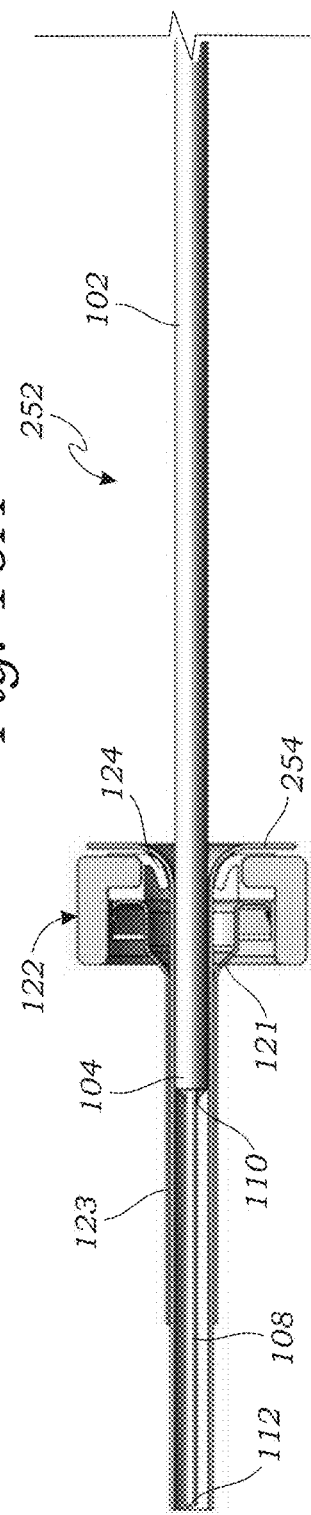
Figure 10C:
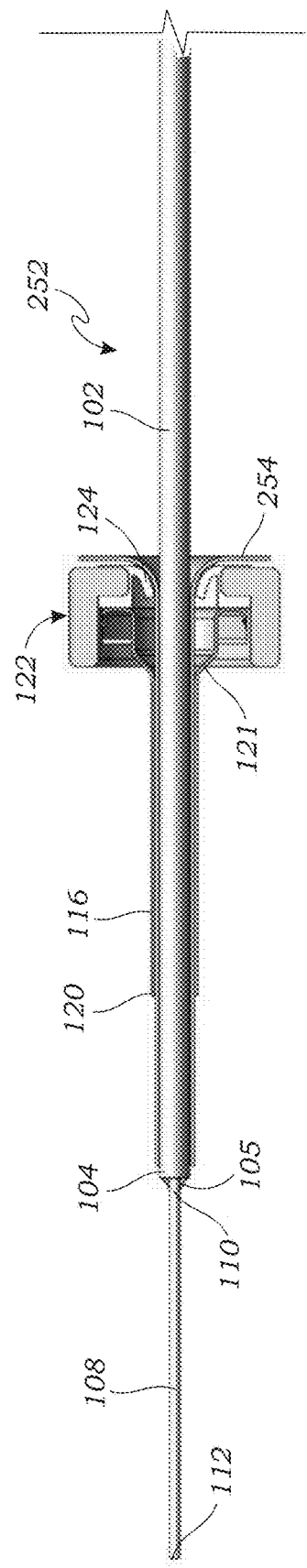

As illustrated in FIGS. 10A-10C, the tip protector tube 116 may be configured to advance fully through the trocar cannula 124, and the handle 254 may function as the protector tube stop 254. The tip protector tube stop 254 is configured to contact a hard stop of the trocar cannula 122, such as the trocar valve 124, or a proximal face of the trocar cannula 122, or other suitable structure of the trocar cannula 122. FIG. 10A shows the injector cannula 252 with the tip protector tube 116 in the extended position. FIG. 10B shows the distal end of the injector cannula 252 (comprising the distal end of 120 of the tip protector tube 116) with the tip protector tube 116 in the extended position being advanced through the trocar valve 124. The tip protector tube 116 protects the injector tip 108 from being damaged as the injector cannula 252 is advance through the trocar valve 124. FIG. 10B also shows the injector cannula 252 as the tip protector tube stop 254 (comprising the handle 254) contacting the hard stop 124 (comprising trocar valve 124). FIG. 10C illustrates the tip protector tube 116 being retracted to the retracted to the retracted position by further advancing the flow cannula 102 and injector tip 108 while the tip protector tube 116 is stopped from further advancement by the cooperating stops 254/124.

Figure 11A:
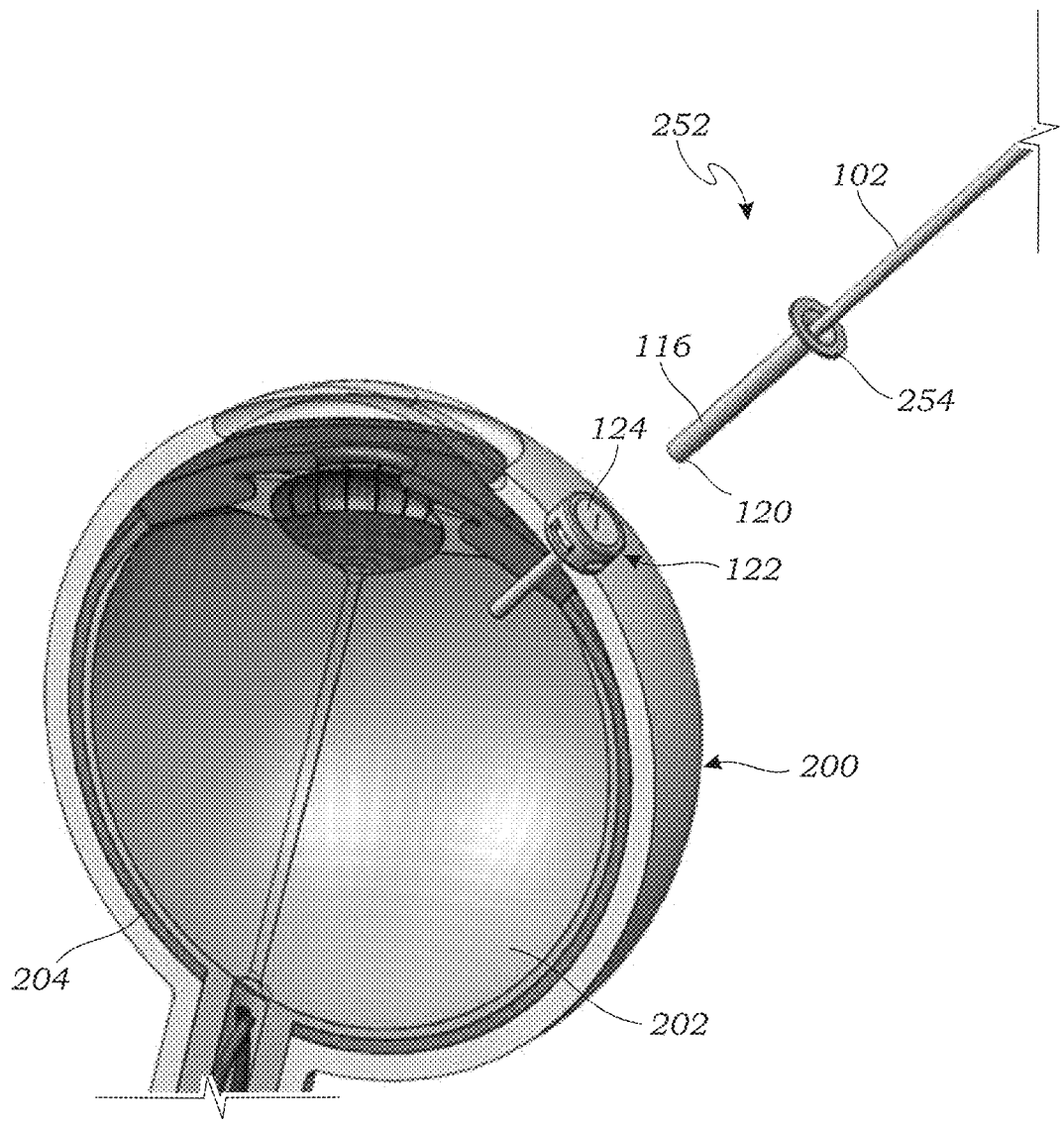
FIGS. 11A-11D are side, cut-away views of a human eye illustrating a method of using the injector cannula of FIGS. 8A-8B for delivering a medicament into a patient's eye, according to one embodiment.

Turning to FIGS. 11A-11D, a method of using the injector cannula 252 to deliver a medicament into a target site of a patient's body will be described. A fluidic injector, such as syringe 300 (see FIG. 15), a self-powered injector 302 (see FIG. 16), or other suitable fluidic injector device, is attached to the Luer hub 138 of the injector fitting 134. As shown in FIG. 11A, a trocar cannula 122 having a trocar valve 124 is inserted into through the outer layers of the eye 200 such that the trocar cannula 122 extends into the vitreous of the eye. The injector cannula 252 is provided with the tip protector tube 116 in the extended position covering and protecting the injector tip 108.

Figure 11B:
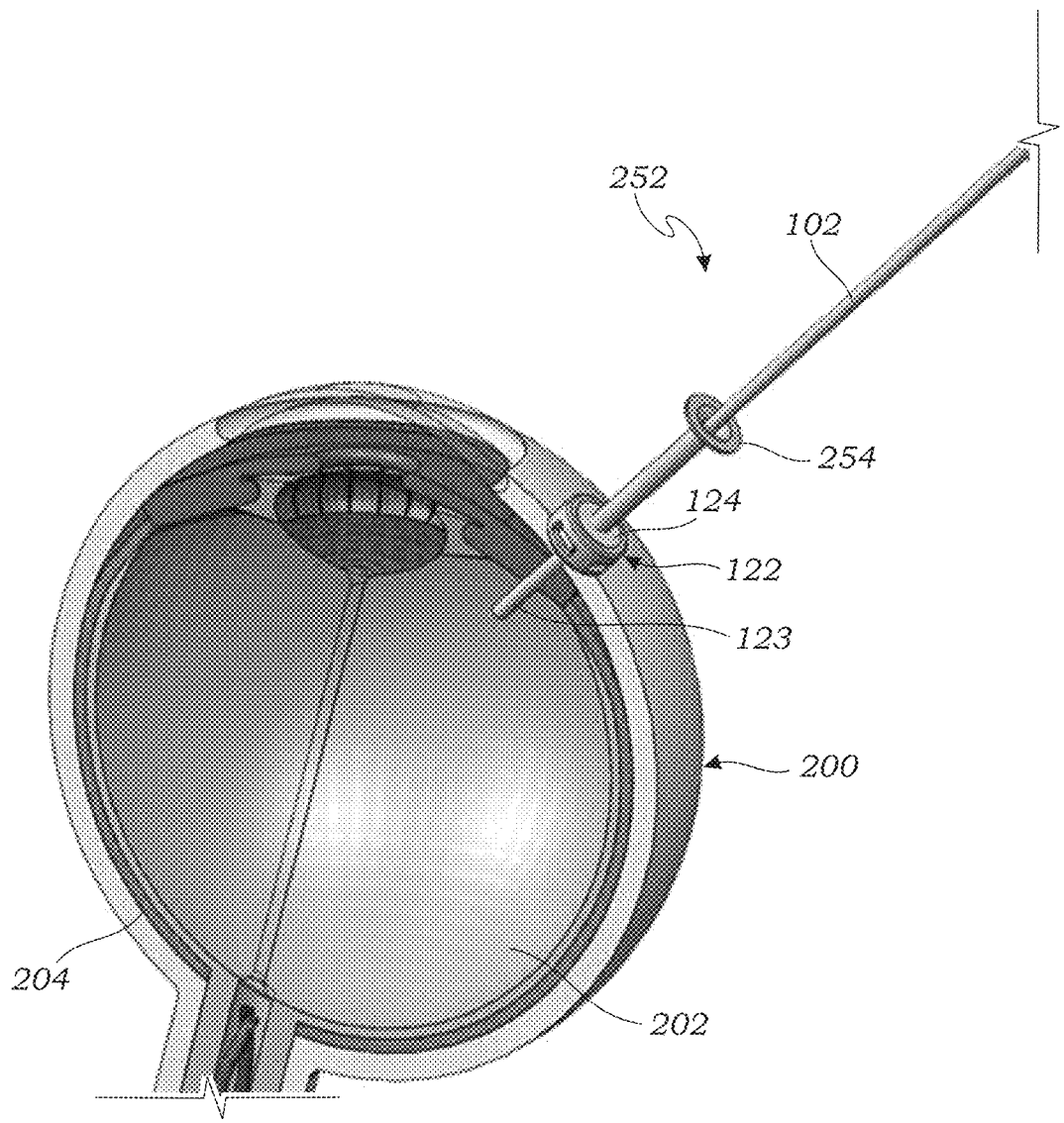
Figure 11C:
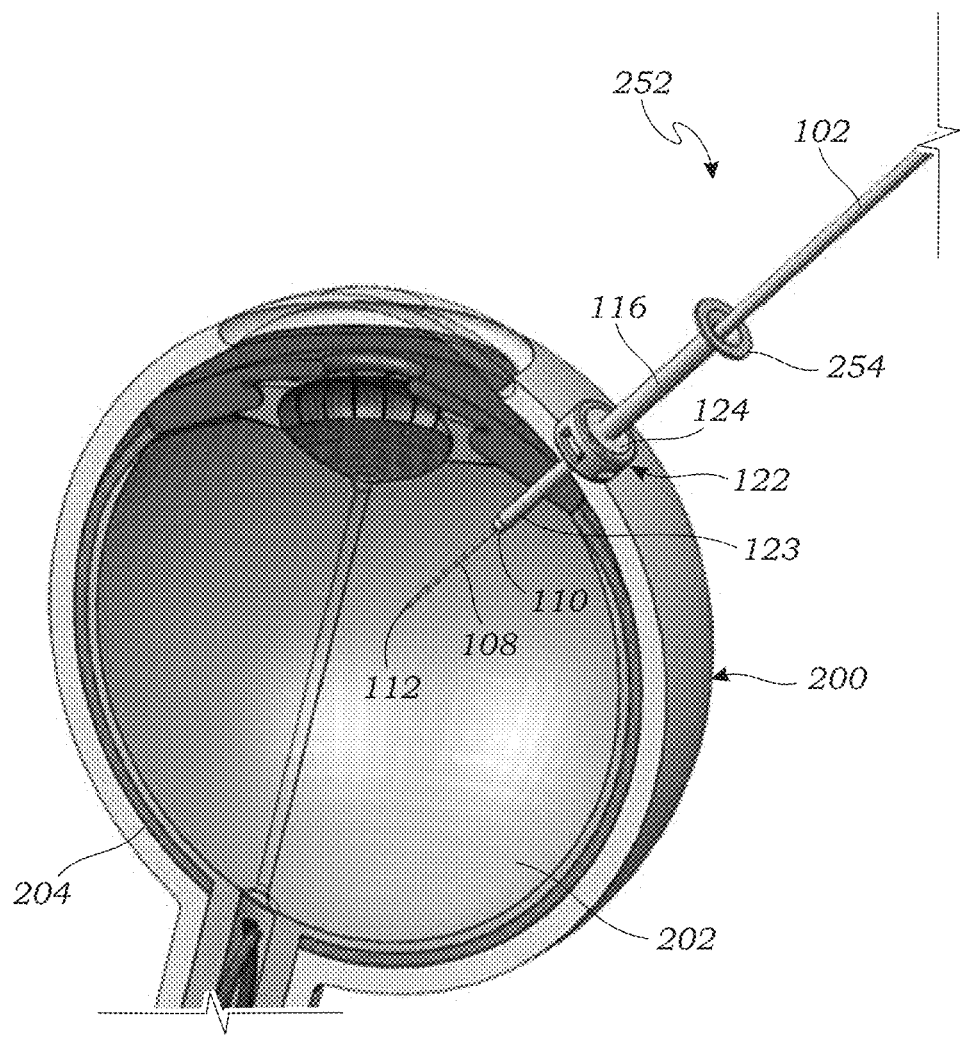

As shown in FIG. 11B, the distal end of the injector cannula 252 (comprising the distal end 120 of the tip protector tube 116) is inserted through the trocar valve 124 and advanced into the vitreous of the eye. The tip protector tube 116 protects the injection tip 108 from being damaged as the injector cannula 100 is advanced through the trocar valve 124. The injector cannula 252 is advanced until the tip protector tube stop 120 (comprising the distal end 120 of the tip protector tube 116) contacts the hard stop 121 (comprising a proximal end of a trocar tube 123 of the trocar cannula 122). As shown in FIG. 11C, the tip protector tube 116 being retracted to the retracted to the retracted position by further advancing the flow cannula 102 and injector tip 108 while the tip protector tube 116 is stopped from further advancement by the cooperating stops 120/121.

Figure 11D:
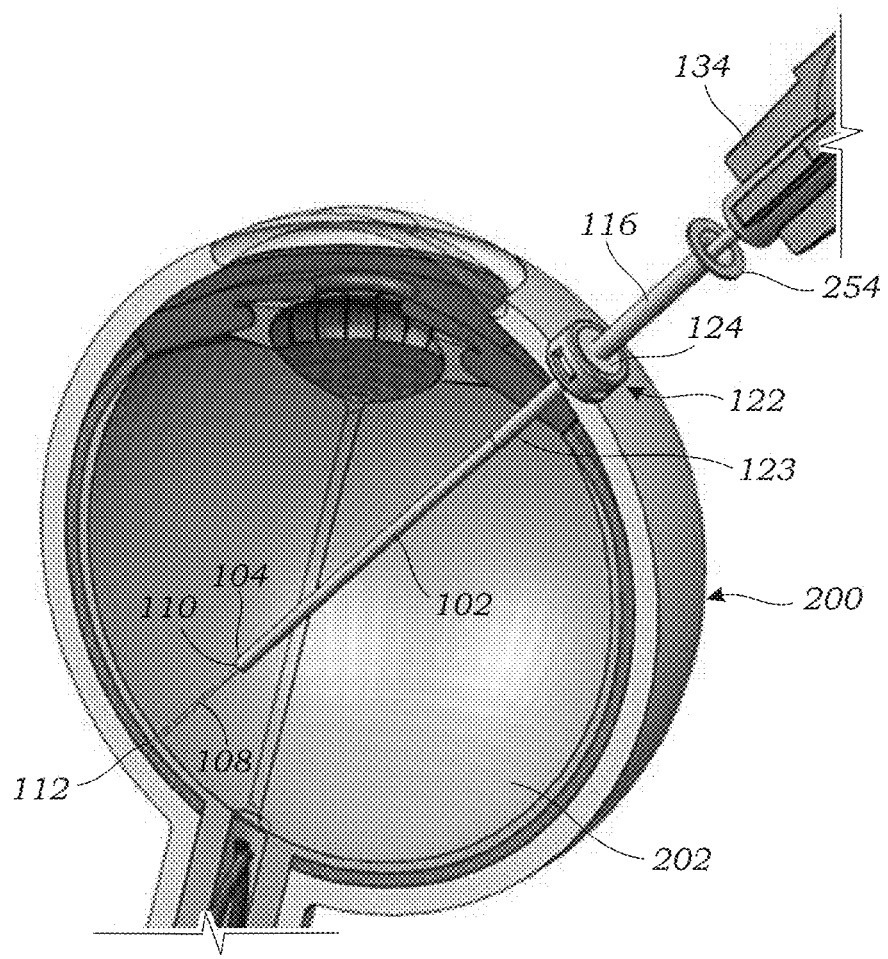

As shown in FIG. 11D, with the tip protector tube 116 in the retracted position, the flow cannula and injector tip 108 are advanced to position the distal end 112 of the injector tip at the target injection site 204, in this example, the sub-retinal space 204. The tip protector tube 116 may pierce body tissue, such as the retina, to position the distal tip 112 at the target injection site 204. The medicament is then injected using the fluidic injector through the flow cannula 102, through the injector tip 108, and into the target injection site 204.

Figure 17A:
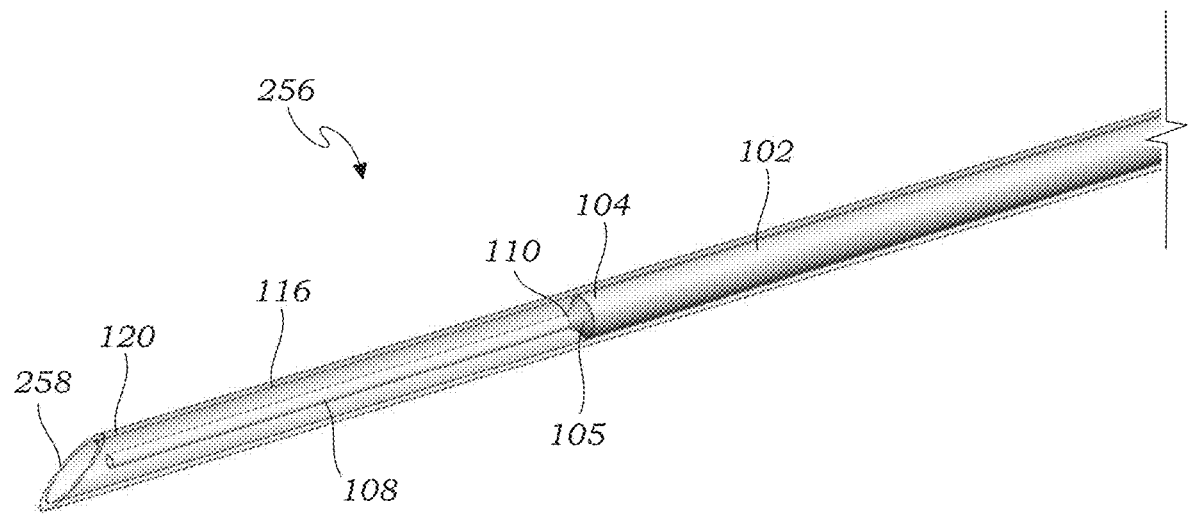
FIG. 17A is a side, perspective view of a distal portion of an injector cannula with a tip protector tube having a hypodermic bevel, in an extended position, according to one embodiment.
Figure 17B:
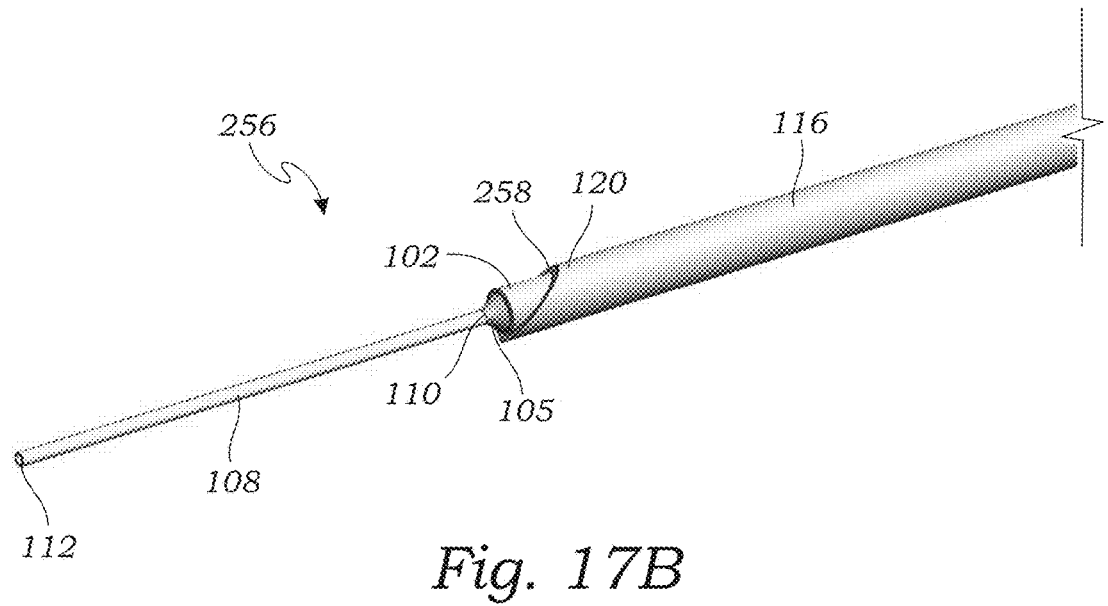
FIG. 17B is a side, perspective view of the distal portion of the injector cannula of FIG. 17A with the tip protector tube retracted to a retracted position, according to one embodiment.

Referring now to FIGS. 17A-17B, another embodiment of an injector cannula 256 is illustrated. The injector cannula 256 is the same as the injector cannula 100, described herein, except that the distal end 120 of the tip protector tube 116 has a hypodermic bevel 258. The hypodermic bevel 256 allows the injector cannula 256 to be used without a trocar cannula 122 (it may also be used with a trocar cannula 122).

The injector cannula 256 may also include a releasable protector tube locking mechanism to lock the tip protector tube 116 in the extended position when using the hypodermic bevel to pierce body tissue, such as the sclera of an eye 200 during a sub-retinal injection procedure, as described herein. The releasable protector tube locking mechanism is releasable to allow the tip protector tube 116 to be retracted to the retracted position. The locking mechanism may be any suitable releasable lock, such as the retention mechanisms described herein, or other lock actuatable by a push button, slide, switch, etc.

Accordingly, a method of using the injector cannula 256 without a trocar cannula 122 to deliver a medicament into a target site of a patient's body is as follows. A fluidic injector, such as syringe 300 (see FIG. 15), self-powered injector 302 (see FIG. 16), or other suitable fluidic injector device, filled with medicament, is attached to the flow cannula 102, such as to a Luer hub 138 of an injector fitting 134 by mating the Luer hub 138 to the Luer hub 139 on the fluidic device. With the hub 144 and tip protector tube 116 locked in the extend position by protector tube locking mechanism as shown in FIG. 17A, the hypodermic bevel 258 is used to pierce body tissue and advance the distal end of the injector cannula 142 (comprising the distal end 120 of the tip protector tube 116) into an anatomical structure. The tip protector tube 116 protects the injector tip 108 from being damaged as the hypodermic bevel 258 and tip protector tube 116 are advanced through the body tissue.

Once the hypodermic bevel 258 is advanced to a desired location in which the injector tip 108 is not at risk of damage, the protector tube locking mechanism is released and the tip protector tube 116 is retracted to the retracted position, thereby exposing the injector tip 108, as shown in FIG. 17B. The flow cannula 102 and injector tip 108 may then be moved to position the injector tip 108 at the target injection site. Then, the fluidic injector is used to inject the medicament through the flow cannula 102, through the injector tip 108, and into the target injection site 204.

The tip protector tube 116 having the hypodermic bevel 258 may be used on any of the injector cannulas disclosed herein, including at least the injector cannulas 130, 142, 172, and 186. The method of using such injector cannulas may then be accomplished without a trocar cannula 122 by modifying them similar to the method of using the injector cannula 256.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. An injector cannula for delivering a medicament into a patient's body, comprising:
   a flow cannula having a proximal end and a distal end;
   an injector fitting attached to the proximal end of the flow cannula such that the distal end of the flow cannula extends distally from the injector fitting, the injector fitting configured to be coupled to a fluidic injector;
   a flexible injector tip disposed on the distal end of the flow cannula and extending distally from the flow cannula;

a tip protector tube slidably disposed on the flow cannula, the tip protector tube slidable on the flow cannula from an extended position in which the tip protector tube covers the entire injector tip, and a retracted position in which the tip protector tube is retracted proximally relative to the injector tip thereby exposing at least part of the injector tip from the tip protector tube, the tip protector tube being substantially stiffer than the injector tip; and a hub permanently attached to a proximal portion of the tip protector tube, the hub slidably disposed on the flow cannula such that retracting the hub proximally retracts the tip protector tube.

2. The injector cannula of claim 1, wherein the injector fitting comprises a Luer hub.

3. The injector cannula of claim 1, further comprising an elastomeric seal disposed on the hub through which the flow cannula passes with a friction fit around the flow cannula.

4. The injector cannula of claim 3, wherein the elastomeric seal is an O-ring seal.

5. The injector cannula of claim 1, wherein the hub has a hub interface and the injector fitting has a fitting interface which mates with the hub interface such that the hub interface and the injector interface secure the hub to the injector fitting in the retracted position of the tip protector tube.

6. The injector cannula of claim 5, wherein the hub interface comprises a female tapered surface and the injector fitting interface comprises a male tapered surface.

7. The injector cannula of claim 1, wherein:
the hub has one or more snaps on the hub, and the injector fitting has a plurality of notches spaced apart longitudinally on the injector fitting, the one or more snaps configured to interface with respective notches of the plurality of notches on the injector fitting to retain the hub and tip protector tube separately in the extended position and the retracted position.

8. The injector cannula of claim 7, wherein:
the hub and the injector fitting have a sliding interface which rotationally aligns the hub and the fitting and prevents relative rotation of the hub and the injector fitting.

9. The injector cannula of claim 8, wherein the sliding interface comprises a slot on one of the hub and the injector fitting and a ridge on the other of the hub and the injector fitting, such that the ridge is slidably received in the slot.

10. The injector cannula of claim 1, wherein:
the hub has a raised feature on an inner diameter surface, and the injector fitting has at least two detents on an outer diameter surface, the raised feature configured to interface with the at least two detents to retain the hub and tip protector tube in two different positions including the extended position and the retracted position.

11. The injector cannula of claim 10, wherein the injector fitting has a groove on the outer diameter surface in which the raised feature is received such that the groove guides the raised feature along a path as the hub is moved relative to the injector fitting.

12. The injector cannula of claim 11, wherein the groove extends in one of the following:
a helical path around the outer diameter surface of the injector fitting;
a linear path extending longitudinally along the outer diameter surface; and
a hook shaped path having a first portion extending circumferentially around the outer diameter surface and a second portion extending longitudinally along the outer diameter surface.

13. The injector cannula of claim 1, wherein one of the hub and the injector fitting as a plurality of ratchet grooves, and the other of the hub and the injector fitting has a one or more retention arms, wherein the retention arms interface with each of the ratchet grooves to retain the hub and tip protector tube in a plurality of different longitudinally spaced apart positions including the extended position and the retracted position.

14. The injector cannula of claim 1, further comprising:
a retraction spring disposed between the hub and the injector fitting, the retraction spring biasing the hub toward the retracted position; and
a locking mechanism between the hub and injector fitting configured to releasably lock the hub in the extended position of the tip protector tube.

15. The injector cannula of claim 14, wherein the locking mechanism comprises a bayonet fitting between the hub and the injector fitting, the bayonet fitting having a locked position which retains the hub in the extended position of the tip protector tube, and an unlocked position which allows the retraction spring to retract the hub and tip protector tube to the retracted position.

16. The injector cannula of claim 1, wherein the flexible injector tip is attached to the proximal end of the flow cannula via a tip bond joint comprising adhesive disposed in an annulus between the injector tip and the flow cannula.

17. The injector cannula of claim 1, further comprising an injector device for providing a pressurized source of medicament coupled to the injector fitting for delivering the medicament through the flow cannula.

18. The injector cannula of claim 17, wherein the injector device is one of a syringe, and a self-powered injector.

19. The injector cannula of claim 1, wherein the tip protector tube comprises a protector tube tip that extends beyond the injector tip in the extended position, the protector tube tip configured to pierce body tissue.

20. The injector cannula of claim 19, wherein the protector tube tip comprises a hypodermic bevel.

21. The injector cannula of claim 19, further comprising a locking mechanism to lock the tip protector tube in the extended position when using the protector tube tip to pierce body tissue, the locking mechanism releasable to allow the tip protector tube to be retracted to the retracted position to expose the at least part of the injector tip.

22. The injector cannula of claim 1, further comprising an injector device for providing a pressurized source of medicament attached to the injector fitting for delivering the medicament through the flow cannula, wherein the tip protector tube is attached to a hub slidable relative to the injector fitting to cause the tip protector tube to slide between the extended position and the retracted position.

23. The injector cannula of claim 22, wherein the injector fitting comprises a connector configured to couple the injector device to the injector fitting.

24. The injector cannula of claim 1, wherein the protector tube is over-molded or bonded to the hub to permanently attach to the protector tube to the hub.

25. An injector cannula for delivering a medicament into a patient's body, comprising:
an injector fitting comprising a first end configured to be coupled to an injector device and a second end;

a flow cannula comprising a proximal end attached to the second end of the injector fitting and a distal end extending distally from the injector fitting;

a flexible injector tip extending distally from the distal end of the flow cannula;

a hub slidably coupled to the injector fitting; and a tip protector tube permanently attached to and extending distally from the hub and slidably disposed over the flow cannula, the hub slidable on the injector fitting to cause the tip protector tube to slide relative to the flow cannula from an extended position in which the tip protector tube covers the entire injector tip, and a retracted position in which the tip protector tube is retracted proximally relative to the injector tip thereby exposing at least part of the injector tip from the tip protector tube, the tip protector tube being substantially stiffer than the injector tip.

26. The injector cannula of claim 25, wherein the hub and the injector fitting have a sliding interface which rotationally aligns the hub and the injector fitting and prevents relative rotation of the hub and injector fitting.

27. The injector cannula of claim 26, wherein the sliding interface comprises one or more longitudinal slots on one of the hub and the injector fitting and one or more longitudinal ridges or fins on the other of the hub and the injector fitting, which are slidably received in respective slots of the one or more longitudinal slots.

28. The injector cannula of claim 25, further comprising a flange on a proximal end of the hub.

29. The injector cannula of claim 25, wherein the hub and the injector fitting comprise features that retain the hub and tip protector tube separately in the extended position and the retracted position, respectively.

30. The injector cannula of claim 29, wherein the features comprise one or more snaps on the hub and a plurality of notches spaced apart longitudinally on the injector fitting, the one or more snaps configured to interface with respective notches on the injector fitting to retain the hub and tip protector tube separately in the extended position and the retracted position.

31. The injector cannula of claim 25, further comprising an injector device for providing a pressurized source of medicament coupled to the first end of the injector fitting for delivering the medicament through the flow cannula.

32. The injector cannula of claim 31, wherein the injector device is one of a syringe, and a self-powered injector.

33. The injector cannula of claim 25, wherein the flexible injector tip has a smaller outer diameter than an outer diameter of the flow cannula.

34. The injector cannula of claim 25, wherein the first end of the injector fitting comprises a connector configured to couple the injector fitting to the injector device.

* * * * *